United States Patent [19]

Anderson et al.

[11] Patent Number: 5,554,634

[45] Date of Patent: Sep. 10, 1996

[54] N-(HYDROXYETHYL)BUTANEDIAMIDE DERIVATIVES

[75] Inventors: Paul C. Anderson, Pierrefonds; Teddy Halmos, St. Laurent; Grace L. Jung, Montréal; Marc-André Poupart; Bruno Simoneau, both of Laval, all of Canada

[73] Assignee: Bio-Mega Boehringer Ingelheim Research Inc., Quebec, Canada

[21] Appl. No.: 432,503

[22] Filed: May 1, 1995

Related U.S. Application Data

[60] Division of Ser. No. 123,954, Sep. 20, 1993, which is a continuation-in-part of Ser. No. 951,250, Sep. 25, 1992, abandoned.

[51] Int. Cl.$^6$ .................... C07D 277/28; C07D 277/38; A61K 31/425
[52] U.S. Cl. .................... 514/370; 548/195; 548/204; 514/365
[58] Field of Search .................... 548/195, 204; 514/370, 616; 564/160

[56] References Cited

FOREIGN PATENT DOCUMENTS 975370  11/1964  United Kingdom .

*Primary Examiner*—Johann Richter
*Assistant Examiner*—Laura L. Stockton
*Attorney, Agent, or Firm*—R. P. Raymond; M-E. M. Devlin; A. R. Stempel

[57] ABSTRACT

Disclosed herein are compounds of the formula:

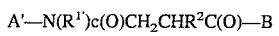

wherein A' is $HO—CR^5(R^6)CH_2$ wherein $R^5$ and $R^6$ together with the carbon atom to which they are attached form a 1,1-(lower cycloalkanediyl); $R^{1'}$ is $R^7R^8NC(O)CH_2$ wherein $R^7$ hydrogen or lower alkyl and $R^8$ is lower alkyl; $R^2$ is, for example, 4-thiazolylmethyl or (2-amino-4-thiazolyl)methyl; and B is a renin substrate transition state mimic, for example, [1(S)-(cyclohexylmethyl)-2(R),3(S)-dihydroxy-5-methylhexyl]amino. The compounds inhibit renin activity and are indicated for the treatment of hypertension and congestive heart failure.

8 Claims, No Drawings

N-(HYDROXYETHYL)BUTANEDIAMIDE DERIVATIVES

This is a division of application Ser. No. 08/123,954, filed Sep. 20, 1993, which is a continuation-in-part of application Ser. No. 07/951,250, filed Sep. 25, 1992, now abandoned.

FIELD OF INVENTION

This invention relates to compounds exhibiting renin inhibiting properties, to processes for producing the compounds, to pharmaceutical compositions thereof, to processes and intermediates for preparing the compounds and to methods of treating renin-dependent hypertension and congestive heart failure.

BACKGROUND OF THE INVENTION

The physiological role of the renin-angiotensin system is to regulate blood pressure and to maintain sodium and volume homeostasis. The key events in this system are the conversion of the polypeptide angiotensinogen to the decapeptide angiotensin I (AI) and the subsequent cleavage of the latter to give the octapeptide angiotensin II (AII). The latter peptide is a potent vasoconstrictor and a potentiator of aldosterone release. Due to potent pressor effects, AII plays a significant role in hypertension and as such has been the target for the development of antihypertensive agents.

One approach to finding such agents is to search for potent inhibitors of the angiotensin converting enzyme. Inter alia, the latter enzyme catalyzes the conversion of AI to AII. This approach has met with success and a number of such agents are used therapeutically to treat hypertension. Another approach is to find specific inhibitors of renin, an aspartyl protease which cleaves angiotensinogen to AI. Since angiotensinogen is the only known natural substrate for renin, this approach has the desirable feature of being aimed at a potential antihypertensive agent with a single mode of action.

In the pursuit of this goal, a great deal of attention has been given to designing renin inhibitors which mimic the natural substrate angiotensinogen. Much of this effort has been focused on the design of analogous substrates incorporating therein a non-cleavable mimic (i.e. a transition state analog) of the renin cleavage site (i.e. Leu-Val) of human angiotensinogen. As a result, a number of potent renin inhibitors have been identified in the laboratory and the ability of renin inhibitors to lower blood pressure and to reduce plasma renin activity has now been demonstrated in the clinic. For a recent review on renin inhibitors, see W. J. Greenlee, Medical Research Reviews, 10, 173 (1990). Nevertheless, progress toward obtaining the ideal renin inhibitor continues to be plagued with problems of low oral absorption, limited bioavailability and rapid elimination, mainly due to the peptidic nature of the inhibitors presently under investigation. Hence, there is a need for a readily administered, effective renin inhibitor.

The renin inhibitors of the present application belong to the class of transition state analog inhibitors of renin. They are characterized by having a N-(2-oxygenated-ethyl)succinamoyl moiety incorporated into their structure. This feature, in combination with their non-peptidic character and their relatively lower molecular weight, apparently contribute beneficially to the stability, absorption and bioavailability of the inhibitors. Another feature of the present inhibitors is their relative specificity for renin as compared to other aspartyl proteases.

The following references exemplify past efforts that have been made in the search for renin inhibitors with improved characteristics:

W. J. Greenlee et al., European patent application 278 158, published Aug. 17, 1988;
A. A. Patchett et al., U.S. Pat. No. 4,839,357, issued Jun. 13, 1989;
D. J. Kempf et al., European patent application 402 646, published Dec. 19, 1990;
P. D. Williams et al., U.S. Pat. No. 5,001,113, issued Mar. 19, 1991;
H. Heitsch et al., Canadian patent application 2,025,093, published Mar. 13, 1991;
W. J. Greenlee et al., U.S. Pat. No. 5,006,511, issued Apr. 9, 1991;
P. D. Williams, Canadian patent application 2,034,524, published July 20, 1991;
H. N. Weller and D. E. Ryono, U.S. Pat. No. 5,055,466, issued Oct. 8, 1991; and
S. H. Rosenberg et al., U.S. Pat. No. 5,063,208, issued Nov. 5, 1991.

SUMMARY OF THE INVENTION

The compounds of the present application are represented by formula 1

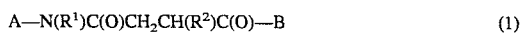

$$A-N(R^1)C(O)CH_2CH(R^2)C(O)-B \qquad (1)$$

wherein

A is an oxygen-bearing radical selected from the group consisting (a) HO—CH($R^3$)CH$_2$ wherein $R^3$ is hydrogen, lower alkyl, lower cycloalkyl, phenyl, benzyl, or an unsubstituted, monosubstituted or disubstituted five- or six-membered heterocyclic ring (hereinafter designated as "Het") containing one or two heteroatoms selected from the group of N, O or S, wherein each substituent is selected independently from the group consisting of lower alkyl, lower alkoxy, halo, hydroxy, amino and lower alkylamino;

(b) HO—CH$_2$CH($R^4$) wherein $R^4$ is lower alkyl, (lower cycloalkyl)-(lower alkyl), phenyl(lower)alkyl or α-hydroxyphenylmethyl;

(c) HO—C$R^5$($R^6$)CH$_2$ wherein each of $R^5$ and $R^6$ is lower alkyl; or $R^5$ and $R^6$ together with the carbon atom to which they are attached form a 1,1-(lower cycloalkanediyl), 1,1-(4-hydroxycyclohexanediyl) or 1,1-(4-oxocyclohexanediyl);

(d) (lower alkoxy)C$R^{5A}$($R^{6A}$)CH$_2$ wherein each of $R^{5A}$ and $R^{6A}$ is lower alkyl; or $R^{5A}$ and $R^{6A}$ together with the carbon atom to which they are attached form a 1,1-(lower cycloalkanediyl); and (e) (lower alkyl)C(O)CH$_2$;

$R^1$ is hydrogen; the oxygen-bearing radical (a), (b) or (c) as defined hereinabove; HO—Alk$^1$—CH$_2$CH$_2$ wherein Alk$^1$ is a divalent alkyl radical containing one to four carbon atoms; (1-8C)alkyl; lower alkyl monosubstituted with lower cycloalkyl, phenyl, 2-(lower alkyl)phenyl, 2-(lower alkoxy)phenyl, 2-halophenyl, 4-(lower alkyl)phenyl, 4-(lower alkoxy)phenyl, 4-halophenyl, (3,4-methylenedioxy)phenyl, 1-naphthyl, 2-naphthyl or Het wherein Het is as defined hereinabove; or $R^7R^8NC(O)CH_2$ wherein (a) $R^7$ is hydrogen or lower alkyl and $R^8$ is hydrogen, lower alkyl or lower alkyl monosubstituted with lower cycloalkyl, phenyl or Het wherein Het is as defined hereinbefore; or (b) $R^7$ is lower alkyl and $R^8$ is $R^9R^{10}$N-Alk$^2$ wherein $R^9$ and $R^{10}$ each independently is hydrogen or lower alkyl and Alk$^2$ is a divalent alkyl radical derived by the removal of two hydrogen atoms, each from a different carbon atom, of a straight or branched chain hydrocarbon containing from two to six carbon atoms; or (c) $R^7$ is lower alkyl and $R^8$ is QC(O) (CH$_2$)$_m$ wherein Q is piperidino, morpholino, thiomorpholino, piperazino or 4-(lower alkyl)-1-piperazinyl and m is the integer 1 or 2; or (d) $R^7$ and $R^8$ together with the nitrogen atom to which they are attached form a pyrrolidino, piperidino, morpholino, thiomorpholino or 4-(lower alkyl)-1-piperazinyl;

$R^2$ is lower alkyl, (lower cycloalkyl)methyl or Het-CH$_2$ wherein Het is as defined hereinabove; and B is a transition state analog of the formula NHCH($R^{11}$)CH(OH)—Z wherein $R^{11}$ is lower alkyl, (lower cycloalkyl)methyl, benzyl, [4-(lower alkyl)phenyl]methyl, [4-(lower alkoxy)phenyl]methyl, or (4-halophenyl)methyl, and Z is lower alkyl, lower cycloalkyl, (lower cycloalkyl)methyl, C(O)OR$^{12}$ wherein $R^{12}$ is lower alkyl, the radical of formula 2

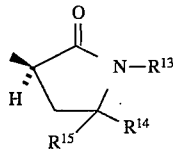

wherein $R^{13}$ is lower alkyl and $R^{14}$ and $R^{15}$ each is hydrogen or lower alkyl, [(1-methyl- 1H-tetrazol-5-yl) thio] methyl or CH(OH)R$^{16}$ wherein $R^{16}$ is lower alkyl or lower cycloalkyl, with the provisos (1) that the asymmetric carbon atom bearing $R^{11}$ has the (S) configuration, (2) that when Z is lower alkyl, lower cycloalkyl, (lower cycloalkyl)methyl or the radical of formula 2 as defined hereinabove then the asymmetric carbon atom bearing the hydroxyl in the NHCH($R^{11}$)CH(OH) radical has the (S) configuration, (3) that when Z is C(O)OR$^{12}$ wherein $R^{12}$ is lower alkyl, or when Z is [(1-methyl-1H-tetrazol-5-yl)thio]methyl, then the asymmetric carbon atom bearing the hydroxyl in the NHCH($R^{11}$)CH(OH) radical has the (R) configuration, (4) that when Z is CH(OH)R$^{16}$ wherein $R^{16}$ is lower alkyl or lower cycloalkyl the asymmetric carbon atoms bearing the hydroxyls in the NHCH($R^{11}$)CH(OH) and Z radicals have respectively the (R) and (S) configuration, and (5) that the carbon atom bearing $R^2$ has the (R) configuration, except when $R^2$ is CH$_2$-Het wherein Het has a nitrogen atom at the point of attachment, and/or has a sulfur atom next to the atom at the point of attachment, of the Het to the methylene (CH$_2$), then in the instance of this exception the carbon atom bearing $R^2$ has the (S) configuration; or a therapeutically acceptable acid addition salt thereof.

A preferred group of compounds of the present invention is represented by formula 1 wherein A is an oxygen-bearing radical selected from the group consisting of:

(a) HO—CH($R^3$)CH$_2$ wherein $R^3$ is hydrogen, lower alkyl, cyclohexyl, phenyl, benzyl or Het wherein Het is as defined hereinabove, (b) HO—CH$_2$CH($R^4$) wherein $R^4$ is cyclohexylmethyl, benzyl or α-hydroxyphenylmethyl, (c) HO—CR$^5$(R$^6$)CH$_2$ wherein $R^5$ and $R^6$ each is lower alkyl, or together with the carbon atom to which they are attached form a 1,1-(lower cycloalkanediyl), 1,1-(4-hydroxycyclohexanediyl) or a 1,1-(4-oxocyclohexanediyl);

(d) (lower alkoxy)CR$^{5A}$(R$^{6A}$)CH$_2$ wherein each of $R^{5A}$ and $R^{6A}$ is lower alkyl; or $R^{5A}$ and $R^{6A}$ together with the carbon atom to which they are attached form a 1,1-(lower cycloalkanediyl); and (e) (lower alkyl)C(O)CH$_2$;

$R^1$ is hydrogen; the oxygen-bearing radical (a), (b) or (c) as defined hereinabove, HO-Alk$^1$—CH$_2$CH$_2$ wherein Alk$^1$ is as defined above; (1–8C)alkyl; lower alkyl monosubstituted with lower cycloalkyl, phenyl, 2-methylphenyl, 4-methylphenyl, 4-methoxyphenyl, 4-chlorophenyl, 4-fluorophenyl, (3,4-methylenedioxy)phenyl, 1-naphthyl, 2-naphthyl or Het wherein Het is as defined hereinabove; or $R^7R^8$NC(O)CH$_2$ wherein (a) $R^7$ is lower alkyl and $R^8$ is lower alkyl or lower alkyl monosubstituted with phenyl or Het wherein Het is as defined hereinabove; or (b) $R^7$ is lower alkyl and $R^8$ is $R^9R^{10}$N-Alk$^2$ wherein $R^9$ and $R^{10}$ each is lower alkyl and Alk$^2$ is as defined hereinabove; or (c) $R^7$ is lower alkyl and $R^8$ is 2-morpholino-2-oxoethyl, 3-morpholino-3-oxopropyl or 3-(4-methyl-1-piperazinyl)-3-oxopropyl; or (d) $R^7$ and $R^8$ together with the nitrogen atom to which they are attached form a pyrrolidino, piperidino, morpholino, thiomorpholino or 4-(lower alkyl)-1-piperazinyl;

$R^2$ is lower alkyl, (lower cycloalkyl)methyl, 1H-imidazol-2-ylmethyl, 1H-imidazol-4-ylmethyl, (1-methyl-1H-imidazol-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazolyl)methyl, [2-(methylamino)-4-thiazol-yl]methyl, 2-pyridinylmethyl or 3-pyridinylmethyl; and B is as defined in the last instance; with the proviso that when A is the oxygen bearing radical (lower alkoxy)CR$^{5A}$(R$^{6A}$)CH$_2$ wherein $R^{5A}$ and $R^{6A}$ are as defined hereinbefore, then $R^1$ is $R^7R^8$NC(O)CH$_2$ wherein $R^7$ and $R^8$ are as defined in the last instance; or a therapeutically acceptable acid addition salt thereof.

A more preferred group of compounds is represented by formula 1 wherein A is 2-hydroxyethyl, (R)- or (S)-2-hydroxypropyl, (R)- or (S)-2-cyclohexyl-2-hydroxyethyl, (R)- or (R,S)-2-hydroxy- 2-phenylethyl, (R)- or (S)-2-cyclohexyl-1-(hydroxymethyl)ethyl, (R)- or (S)-(1-hydroxymethyl)-2-phenylethyl, (1S,2S)-2-hydroxy-1-(hydroxymethyl)-2-phenylethyl, 2-hydroxy-2-(2-pyridinyl)ethyl; HO—CR$^5$(R$^6$)CH$_2$ wherein $R^5$ and $R^6$ each is lower alkyl, or $R^5$ and $R^6$ together with the carbon atom to which they are attached form a 1,1-cyclopentanediyl, 1,1-cyclohexanediyl, 1,1-cycloheptanediyl, 1,1-cyclooctanediyl, 1,1-(4-oxo-cyclohexanediyl) or 1,1-(4-hydroxycyclohexanediyl); (lower alkoxy)CR$^{5A}$(R$^{6A}$)CH$_2$ wherein each of $R^{5A}$ and $R^{6A}$ is lower alkyl or $R^{5A}$ and $R^{6A}$ together with the carbon atom to which they are attached form a 1,1-cyclopentanediyl, 1,1-cyclohexanediyl, 1,1-cycloheptanediyl or 1,1-cyclooctanediyl; 2-oxopropyl, 2-oxobutyl or 3-methyl-2-oxobutyl; $R^1$ is hydrogen; HO—CH($R^3$)CH$_2$ wherein $R^3$ is hydrogen or lower alkyl; HO—CR$^5$(R$^6$)CH$_2$ where R$^5$ and R$^6$ together with the carbon atom to which they are attached form a 1,1-cyclohexanediyl or a 1,1-cycloheptanediyl; 3-hydroxypropyl; methyl; ethyl; propyl; 2-methylpropyl; 2-ethylbutyl; 1-propylbutyl; 2-propylpentyl; cyclopropylmethyl; cyclopentylmethyl; cyclohexylmethyl; cycloheptylmethyl; cyclooctylmethyl; benzyl; 2-phenylethyl; 3-phenylpropyl; [(3,4-methylenedioxy)phenyl]methyl; 1-naphthylmethyl; 2-pyrrolylmethyl; 1H-imidazol-2-ylmethyl; 1H-imidazol-4-ylmethyl; 2-furanylmethyl; (2-methylphenyl)methyl; 2-thienylmethyl; 2-oxazolylmethyl; 2-thiazolylmethyl; 4-thiazolylmethyl; (2-amino-4-amino-4-thiazolyl)methyl; (4-amino-2-thiazolyl)methyl; 2-pyridinylmethyl; 3-pyridinylmethyl; 4-pyridinylmethyl; 2-pyridinylethyl; or R$^7$R$^8$NC(O)CH$_2$ wherein R$^7$ is methyl or ethyl and R$^8$ is methyl, ethyl, 2-(dimethylamino)ethyl, 2-(diethylamino)-ethyl, or Het-(CH$_2$)$_n$ wherein Het is 2-pyrrolyl, 2-furanyl, 2-thienyl, 1H-imidazol-2-yl, 1H-imidazol-4-yl, 2-isoxazolyl, 2-thiazolyl, 4-thiazolyl, 2-pyridinyl, 3-pyridinyl, 4-pyridinyl, morpholino, 4-methyl-1-piperazinyl or 2-pyrimidyl and n is the integer 1 or 2; or R$^7$ is methyl and R$^8$ is 3-morpholino-3-oxopropyl or 3-(4-methyl-1-piperazinyl)-3-oxopropyl; or R$^7$ and R$^8$ together with the nitrogen to which they are attached form a pyrrolidino, piperidino, morpholino or 4-methyl-1-piperazinyl; R$^2$ is propyl, 2-methylpropyl, cyclopropylmethyl, cyclopentylmethyl, cyclohexylmethyl, 1H-imidazol-2-ylmethyl, 1H-imidazol-4-ylmethyl, (1-methyl-1H-imidazol-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazolyl)methyl, [2-methylamino)-4-thiazolyl]methyl or 3-pyridinylmethyl; and B is [1(S)-(2-methylpropyl)-2(S)-hydroxy-5-methylhexyl]amino, [1(S)-(cyclohexylmethyl)-2(S)-hydroxy- 5-methylhexyl]amino, {1(S)-[(4-methoxylphenyl)methyl]-2(S)-hydroxy-5-methylhexyl}amino, [1(S)-(cyclohexylmethyl)- 2(S)-hydroxy-4-methylpentyl] amino, [1(S)-(cyclohexylmethyl)-2(S)-hydroxy-(3-cyclopropylpropyl)]amino, [1(S)-(2-methylpropyl)-2(R),3(S)-dihydroxy-5-methylhexyl]amino, [1(S)-(cyclohexylmethyl)-2(R),3(S)-dihydroxy-5-methylhexyl]amino, {1(S)-[(4-methoxyphenyl)methyl]-2(R),3(S)-dihydroxy-5-methylhexyl}amino, [1(S)-(2-methylpropyl)-2(R),3(S)-dihydroxy-(3-cyclopropylpropyl)]amino, [1(S)-(cyclohexylmethyl)-2(R),3(S)-dihydroxy-(3-cyclopropylpropyl)] amino, [1(S)-(phenylmethyl)-2(R),3(S)-dihydroxy-(3-cyclopropylpropyl)]amino, {1(S)-[(4-methoxyphenyl)methyl]-2(R),3(S)-dihydroxy(3-cyclopropylpropyl)}amino, [1(S)-(cyclohexylmethyl)-2(R)-hydroxy-3-(1-methylethoxy)-3-oxopropyl]amino, [1(S)-(cyclohexylmethyl)-2(S)-hydroxy-2-(1,5,5-trimethyl-2-oxopyrrolidin-3(S)-yl)ethyl]amino or {1(S)-(cyclohexylmethyl)-2(R)-hydroxy-3-[(1-methyl-1H-tetrazol-5-yl)thio]propyl}amino; or a therapeutically acceptable acid addition salt thereof.

A most preferred group of compounds is represented by formula 1 wherein A is 2-hydroxyethyl, (R)- or (S) -2-hydroxypropyl, (R)- or (S)-2-cyclohexyl-2-hydroxyethyl, (R)-2-hydroxy-2-phenylethyl, (S)-1-(hydroxymethyl)-2-phenylethyl, (1S,2S)-2-hydroxy-t-(hydroxymethyl)-2-phenylethyl, 2-hydroxy-2-methylpropyl, (1-hydroxycyclohexyl)methyl, (1-hydroxycycloheptyl)methyl, (1-hydroxycyclooctyl)methyl, (1-methoxycyclopentyl)methyl, (1-methoxycyclohexyl)methyl, (1-methoxycycloheptyl)methyl or (1-methoxycyclooctyl)methyl; R$^1$ is hydrogen, methyl, ethyl, propyl, 2-methylpropyl, 2-ethylbutyl, 1-propylbutyl, 2-propylpentyl, 2-hydroxyethyl, cyclopropylmethyl, cyclopentylmethyl, cyclohexylmethyl, cycloheptylmethyl, cyclooctylmethyl, benzyl, [(3,4-methylenedioxy)phenyl]methyl, 1H-imidazol- 2-ylmethyl, 2-furanylmethyl, (2-methylphenyl)methyl, 2-pyridinylmethyl, 3-pyridinylmethyl, 4-pyridinylmethyl, 2-(2-pyridinyl)ethyl, 2-(dimethylamino)- 2-oxoethyl, 2-{methyl[2-(2-pyridinyl)ethyl]amino}-2-oxoethyl or 2-{methyl[2-(3-pyridinyl)ethyl]amino}-2-oxoethyl; R$^2$ is propyl, cyclopropylmethyl, 1H-imidazol-4-ylmethyl, (1-methyl-1H-imidazol- 4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl or (2-amino- 4-thiazolyl)methyl; and B is [1(S)-(cyclohexylmethyl)- 2(S)-hydroxy-4-methylpentyl]amino, [1(S)-(cyclohexylmethyl)-2(S)-hydroxy-(3-cyclopropylpropyl)]amino, [1(S)-(cyclohexylmethyl)-2(R),3(S)-dihydroxy- 5-methylhexyl]amino, [1(S)-(cyclohexylmethyl)-2(R),3(S)-dihydroxy-(3-cyclopropylpropyl)]amino, [1(S)-(cyclohexylmethyl)-2(R)-hydroxy-3-(1-methylethoxy)- 3-oxopropyl] amino or [1(S)-(cyclohexylmethyl)- 2(S)-hydroxy-2-(1,5,5-trimethyl-2-oxopyrrolidin- 3(S)-yl)ethyl]amino; or a therapeutically acceptable acid addition salt thereof.

Included within the scope of this invention is a pharmaceutical composition for treating renindependent hypertension comprising a compound of formula 1, or a therapeutically acceptable acid addition salt thereof, and a pharmaceutically acceptable carrier.

Also included in this invention is a method of treating renin-dependent hypertension or congestive heart failure in a mammal comprising administering thereto a blood pressure-lowering effective amount of the compound of formula 1, or a therapeutically acceptable acid addition salt thereof.

Processes for preparing the compounds of formula 1 are described hereinafter.

Details of the Invention

GENERAL

With reference to the instances where (R) or (S) is used to designate the configuration of a radical, e.g. R$^1$ of the compound of formula 1, the designation is done in the context of the compound and not in the context of the radical alone.

The term "Alk$^1$" as used herein means a divalent alkyl radical derived by the removal of two hydrogen atoms from a straight or branched chain aliphatic hydrocarbon containing from one to four carbon atoms and includes, for example, —CH$_2$—, —CH$_2$CH$_2$—, —CH$_2$CH$_2$CH$_2$—, —CH(CH$_3$)CH$_2$CH$_2$— and —CH$_2$CH(C$_2$H$_5$)—.

The term "Alk$^2$" as used herein means a divalent alkyl radical derived by removal of two hydrogen atoms, each from a different carbon atom, of a straight or branched chain aliphatic hydrocarbon containing from two to six carbon atoms and includes, for example, —CH$_2$CH$_2$—, —CH$_2$CH$_2$CH$_2$—, —CH(CH$_3$)CH$_2$CH$_2$— and —(CH$_2$)$_6$—.

The term "lower alkyl" as used herein, either alone or in combination with a radical, means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl and 1,1-dimethylethyl.

The term "(1–8C)alkyl" as used herein means straight and branched chain alkyl radicals containing from one to eight carbon atoms and includes ethyl, butyl, 1-methylpropyl, 1-ethylpropyl, 1-ethylbutyl, 2-ethyl-2-methylbutyl, 2-ethylbutyl, 1-propylbutyl, 2-propylpentyl and the like.

The term "lower cycloalkyl" as used herein, either alone or in combination with a radical, means saturated cyclic hydrocarbon radicals containing from three to ten carbon atoms and includes cyclopropyl, cyclobutyl, cyclopentyl, cyclohexyl, cycloheptyl and cyclooctyl.

The term "1,1-(lower cycloalkanediyl)" means a divalent cycloalkyl radical containing from three to ten carbon atoms, derived by the removal of two hydrogen atoms from the same carbon atom of a corresponding saturated cyclic hydrocarbon and includes, for example, 1,1-cyclopentanediyl, 1,1-cyclohexanediyl, 1,1-cycloheptanediyl and 1,1-cyclooctanediyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "halo" as used herein means a halo radical selected from bromo, chloro, fluoro or iodo.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, lower alkyl, lower alkoxy, halo, amino or lower alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)thiazole, piperidine, 1-methylpiperazine, 1,4-dioxane, morpholine, pyridine, pyrimidine and 2,4-dimethylpyrimidine.

The term "α-hydroxyphenylmethyl" as used herein means a phenylmethyl radical bearing a hydroxy substituent on the methylene portion thereof. The radical can be represented by the symbol PhCH(OH).

The term "coupling agent" as used herein means an agent capable of effecting the dehydrative coupling of a carboxy group of one compound with a free amino group of another compound to form an amide bond between the reactants. The agents promote or facilitate the dehydrative coupling by activating the carboxy group. Descriptions of such coupling agents and activated groups are included in general textbooks of peptide chemistry; for instance, E. Schröder and K. L. Lübke, "The Peptides", Vol. 1, Academic Press, New York, N.Y., 1965, pp 2–128, and "The Peptides: Analysis, Synthesis, Biology", E Grass et al , Eds., Academic Press, New York, N.Y., U.S.A., 1979–1987, Volumes 1 to 9. Examples of suitable coupling agents are 1,1'-carbonyldiimidazole or N,N'-dicyclohexylcarbodiimide. Other examples are 1-hydroxybenzotriazole in the presence of N,N'-dicyclohexylcarbodiimide or N-ethyl-N'-[(3-dimethylamino)propyl]carbodiimide. A very practical and useful coupling agent is the commercially available (benzotriazol-1-yloxy)tris(dimethylamino)-phosphonium hexafluorophosphate, either by itself or in the presence of 1-hydroxybenzotriazole. Still another very practical and useful coupling agent is the commercially available 2-(1H-benzotriazol-1-yl)-N,N,N',N'-tetramethyluronium tetrafluoroborate.

The term "pharmaceutically acceptable carrier" as used herein means a non-toxic, generally inert vehicle for the active ingredient, which does not adversely affect the ingredient.

The term "effective amount" as used herein means a predetermined amount of the compound of formula 1 sufficient to lower blood pressure on being administered to a mammal.

Process

In general, the compounds of formula 1 are prepared by known methods using reaction conditions which are known to be suitable for the reactants. Description of the methods are found in standard textbooks such as "Annual Reports In Organic Synthesis–1990", K. Turnbull et al., Eds, Academic Press, Inc., San Diego, Calif., U.S.A., 1990 (and the preceding annual reports), "Vogel's Textbook Of Practical Organic Chemistry", B. S. Furniss et al., Eds, Longman Group Limited, Essex, UK, 1986, and "The Peptides: Analysis, Synthesis, Biology", E. Grass et al., Eds, Academic Press, New York, N.Y., U.S.A., 1979–1987, Volumes 1 to 9.

Since the compounds of formula 1 contain two amide bonds, a convenient and practical approach to preparing the compounds is based on the stepwise coupling of the appropriate fragments, i.e. precursors for the amide bond formations.

A common feature of the coupling of the fragments, which involves the reaction of a free amino function of one fragment with a free carboxy function of another fragment, is the protection of competing reactive sites, if present, on the fragments. Such protection is provided by the use of known protective groups which will prevent a chemical reaction from occurring at the competing site during the coupling step and which can ultimately be removed after completion of the coupling to afford the desired product. The protective groups and the deprotecting agents for removing the group are selected according to conventional practice. See J. W. Greene and P. G. M. Wuts, "Protective Groups In Organic Synthesis", 2nd ed., John Wiley & Sons, Inc., New York, N.Y., U.S.A., 1991 for a full description of protective groups and deprotective agents.

More explicitly, a process for preparing the compounds of formula 1, involving the stepwise coupling of appropriate fragments (i.e. reactants) in which competing reactive sites, if present, are protected by suitable protective groups, comprises:

(a) coupling a monoprotected dicarboxylic acid of formula 2

$$W^1\text{---}C(O)CH_2CH(R^2)C(O)OH \qquad 2$$

wherein $W^1$ is a carboxy protecting group and $R^2$ is as defined hereinbefore with an amine of formula H—B wherein B is as defined herein to obtain the corresponding protected amido acid of formula 3

$$W^1\text{---}C(O)CH_2CH(R^2)C(O)\text{---}B \qquad 3$$

wherein $W^1$, $R^2$ and B are as defined hereinbefore;

(b) reacting the latter compound with a deprotecting agent to obtain the corresponding amido acid of formula 4

$$HO\text{---}C(O)CH_2CH(R^2)C(O)\text{---}B \qquad 4$$

wherein $R^2$ and B are as defined hereinbefore; and (c) coupling the latter amido acid with an amine of formula $ANH(R^1)$ wherein A and $R^1$ are as defined hereinbefore; and, if required, eliminating any protective groups from the instant product, to obtain the corresponding compound of formula 1.

Alternatively, the compounds of formula 1 can be prepared by an analogous process comprising:

(d) coupling an amine of formula $ANH(R^1)$ in which A and $R^1$ are as defined hereinbefore with a monoprotected dicarboxylic acid of formula 5

$$HO\text{---}C(O)CH_2CH(R^2)C(O)\text{---}W^2 \qquad 5$$

wherein $R^2$ is as defined herein and $W^2$ is a carboxy protective group to obtain the corresponding protected amido acid of formula 6

$$A\text{—}N(R^1)C(O)CH_2CH(R^2)C(O)\text{—}W^2 \qquad 6$$

wherein A, $R^1$, $R^2$ and $W^2$ are as defined hereinbefore;

(e) reacting the latter compound with a deprotecting agent to obtain the corresponding amido acid of formula 7

$$A\text{—}N(R^1)C(O)CH_2CH(R^2)C(O)\text{—}OH \qquad 7$$

wherein A, $R^1$ and $R^2$ are as defined hereinbefore; and (f) coupling the latter amido acid with an amine of formula H—B wherein B is as defined hereinbefore; and, if required, eliminating any protective groups from the instant product, to obtain the corresponding compound of formula 1.

Note that with respect to the preceding compounds of formulae 2 to 7, inclusive, the aforementioned provisos regarding the stereochemistry of B and $R^2$ apply as well to the corresponding carbon atoms of these compounds.

Examples of suitable carboxy protective groups for the preceding processes are phenylmethoxy (benzyloxy), (4-nitrophenyl)methoxy, 9-fluorenylmethoxy and tert-butoxy. Note also that a 4-substituted- 2-oxazolidinone group, arising from the use of an "Evans' chiral auxiliary" to prepare the monoprotected dicarboxylic acids 2 and 5 as described hereinafter, can be used as a carboxy protective group.

The requisite starting materials of formula 2 and formula 5 can be prepared by processes designed to give the desired stereochemistry. Convenient and practical processes for preparing the starting materials involve the application of the stereoselective alkylation method of D. A. Evans et al., J. Amer. Chem. Soc., 103, 2127 (1981) and J. Amer. Chem. Soc., 104, 1737 (1982). Such a process is illustrated by the following scheme directed to the preparation of the protected carboxylic acid 2 wherein $R^2$ is as defined herein, $W^1$ is tert-butoxy or phenylmethoxy (the carboxy protective group) and U is 1-methylethyl or benzyl.

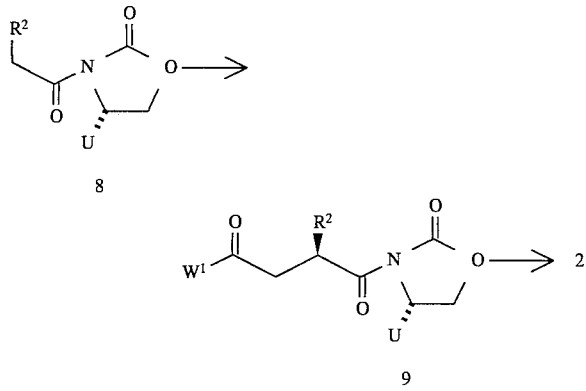

Accordingly, the chiral imide 8 is alkylated with tert-butyl α-bromoacetate or benzyl α-bromoacetate to afford the protected imide 9. Subsequent reaction of latter compound with lithium hydroxide-hydrogen peroxide gives the monoprotected dicarboxylic acid of formula 2 in which $R^2$ and $W^1$ are as defined in the last instance.

In turn, the chiral imide 8 can be prepared by acylating the "Evans' chiral auxiliary", (S)-4-(1-methylethyl)- 2-oxazolidinone or (S)-4-(phenylmethyl)-2-oxazolidinone, with the corresponding acid of formula $R^2CH_2COOH$ or a precursor acid capable of being transformed to the chiral imide 9.

An analogous process can be used to prepare the monoprotected dicarboxylic acids of formula 5.

A convenient and practical process is realized for example simply removing the carboxy protective group $W^1$ from the previously noted protected imide 9 whereby the desired monoprotected dicarboxylic acid of formula 5 is obtained. In this instance, the chiral auxiliary, e.g. the N-substituted 4(S)-(1-methylethyl)- 2-oxazolidinone, assumes a new role as the carboxy protective group $W^2$.

Processes for preparing the monoprotected dicarboxylic acids of formulae 2 and 5 are illustrated in the examples hereinafter.

The amines of formula $ANH(R^1)$ comprise (a) aminoethanols, i.e. amines of formula $ANH(R^1)$ wherein A is the oxygen-bearing radical selected from the group consisting of $HO\text{—}CH(R^3)CH_2$, $HO\text{—}CH_2CH(R^4)$ and $HO\text{—}CR^5(R^6)CH_2$ wherein $R^3$, $R^4$ and $R^5$ and $R^6$ are as defined herein, and $R^1$ is as defined herein, (b) alkoxyalkylamines of formula $ANH(R^1)$ wherein A is the oxygen-bearing radical (lower alkoxy)—$CR^{5A}(R^{6A})CH_2$ wherein $R^{5A}$ and $R^{6A}$ are as defined herein and $R^1$ is defined herein, and (c) aminoketones, i.e. amines of formula $ANH(R^1)$ in which A is (lower alkyl)$C(O)CH_2$ and $R^1$ is as defined herein.

The aforementioned aminoethanols are either known or can be prepared by standard methods for preparing β-aminoalcohols. See, for example, the aminolysis of epoxides methods described by L. E. Overman and L. A. Flippin, Tetrahedron Lett., 22, 195 (1981) and M. Chini et al., Tetrahedron Lett., 31, 4661 (1990), or the reductive amination methods described by S. G. Wilkinson in "Comprehensive organic Chemistry", D. Barton and W. D. Ollis, Eds, Pergamon Press, Oxford, UK, Vol. 2, pp 3–11, 1979. Typical preparations of various amines of formula $ANH(R^1)$ are described in the examples.

The aforementioned alkoxyalkylamines can be prepared by known methods for preparing β-alkoxyalkylamines such as the O-alkylation of the previously noted β-amino-alcohols or their corresponding amino protected derivatives [e.g. tertiary-butyloxycarbonyl (Boc) derivatives].

A noteworthy group of the alkoxyalkylamines are those of formula (lower alkoxy)$CR^{5A}R^{6A}CH_2N(R^1)H$ wherein $R^{5A}$ and $R^{6A}$ are as defined herein and $R^1$ is $R^7R^8NC(O)CH_2$ wherein $R^7$ and $R^8$ are as defined herein. They are noteworthy because they can be transformed by the processes described herein to a preferred group of compounds of formula 1 in which A is (lower alkoxy)$CR^{5A}R^{6A}CH_2$ and $R^1$ is $R^7R^8NC(O)CH_2$ as defined herein, and $R^2$ and B are as defined herein. A practical method for preparing this group of alkoxyalkylamines involves the condensation of the β-alkoxyamine of formula (lower alkoxy)$CR^{5A}R^{6A}CH_2NH_2$ in which $R^{5A}$ and $R^{6A}$ are as defined herein with benzyl bromoacetate, hydrolysis of the subsequently prepared Boc derivative of the condensation product to give the corresponding acid [i.e. (lower alkoxy)$CR^{5A}R^{6A}CH_2N(Boc)CH_2C(O)OH$] and subsequent coupling of the latter acid with the appropriate amine of formula $R^7R^8NH$ in which $R^7$ and $R^8$ are as defined herein to give the desired alkoxyalkylamine after removal of the Boc protecting group. The method for preparing this group of alkoxyalkylamines in this manner is illustrated by example 1K hereinafter.

The aforementioned aminoketones, likewise, are known or can be prepared by standard methods. For example, the appropriate Boc protected acetaldehyde derivative (O)CHN-(tert-butyloxycarbonyl)$R^1$ can be reacted with the appropriate Grignard reagent of formula A—Mg—X wherein A is lower alkyl and X is bromo or chloro to give the corresponding secondary alcohol of the desired aminoketone.

Subsequent oxidation of the secondary alcohol affords the aminoketone. A typical preparation of such an aminoketone is described in example 1L hereinafter.

The amines of formula H—B in which B is as defined hereinbefore are known, having been described by K. Nakano et al., European patent application 281 316, published Sep. 7, 1988, J. R. Luly et al., U.S. Pat. No. 4,845,079, issued Jul. 4, 1989, B. Quirico et al., European patent application 332 008, published Sep. 13, 1989, K. Hemmi et al., U.S. Pat. No. 4,963,530, issued Oct. 16, 1990, P. D. Williams et al., J. Med. Chem. 34. 887 (1991) and F. Matsuda et al., Bull. Chem. Soc. Jpn., 65, 360 (1992).

In the instance where a particular compound of formula 1 has a residue which functions as a base, the compound can be obtained in the form of a therapeutically acceptable acid addition salt. Examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In general, the therapeutically acceptable salts of the compounds of formula 1 are biologically fully equivalent to the peptides themselves.

Biological

The compounds of formula 1 possess the ability to inhibit renin activity. The renin inhibiting activity and enzyme specificity of the compounds can be demonstrated in standard pharmacological tests such as those described by J. R. Luly et al., Biochem. Biophys. Res. Comm., 143, 44 (1987).

In vitro renin inhibiting activity for the compounds has been demonstrated in the plasma renin assay, see example 6 hereinafter.

Primates (e.g. marmosets, cynomolgus monkeys and baboons) are a preferred species for demonstrating in vivo activity for renin inhibitors, because there is substantial homology in the sequence of primate renin and human renin. In this connection, compounds of this invention have shown blood pressure lowering effects when the compounds were administered intravenously or orally to sodium-depleted cynomolgus monkeys, pretreated 18 hours before with an intramuscular injection (2.5 mg/kg) of furosemide to stimulate endogenous renin secretion.

Accordingly, the compounds are indicated the diagnosis, prophylaxis and treatment of renin-associated hypertension in mammals including humans, primates, horses and dogs. The compounds also can be used for treating congestive heart failure in mammals including humans, primates, horses and dogs. For the latter purposes or indications, the compounds can be administered orally or parenterally in a vehicle comprising one or more pharmaceutically acceptable carriers, the proportion of which is determined by the solubility and chemical nature of the compounds, chosen route of administration and standard biological practice. For oral administration, the compound can be formulated in unit dosage forms such as capsules or tablets each containing a predetermined amount of the active ingredient, ranging from about 25 to 250 mg, in a pharmaceutically acceptable carrier.

For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g. in "Remington's Pharmaceutical Sciences", 18th ed, Mack Publishing Company, Easton, Penn., 1990.

The dosage of the compound will vary with the form of administration and the particular active agent chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound is most desirably administered at a concentration level that will lower blood pressure without causing any harmful or deleterious side effects.

For oral administration, the compound is administered in the range of 1.0 to 50 mg per kilogram of body weight per day, with a preferred range of 1.0 to 30 mg per kilogram per day.

With reference to systemic administration, the compound of formula 1 is administered at a dosage of 0.1 mg to 5.0 mg per kilogram of body weight per day, although the aforementioned variations will occur. However, a dosage level that is in the range of from about 0.1 mg to 1.0 mg per kilogram of body weight per day is most desirably employed in order to achieve effective results.

The following examples illustrate further this invention. Temperatures are given in degrees Celsius. Solution percentages or ratios express a volume to volume relationship, unless stated otherwise. Nuclear magnetic resonance spectra were recorded on a Bruker 200 MHz or 400 MHz spectrometer (a 400 MHz spectrum being noted as such in the preamble of the spectrum); the chemical shifts ($\delta$) are reported in parts per million. The concentrations for the optical rotations are expressed in grams of the compound per 100 mL of solution. Abbreviations or symbols used in the examples include Boc: t-butyloxycarbonyl; BOP•$PF_6$: (benzotriazol-1-yloxy)tris (dimethylamino)phosphonium hexafluorophosphate; $CH_2Cl_2$, methylenedichloride; DMAP: 4-(dimethylamino)pyridine; DIPEA: diisopropylethylamine; DMF: dimethylformamide; EtOH: ethanol; EtOAc: ethyl acetate; $Et_2O$: diethyl ether; FAB/MS: fast atom bombardment mass spectrometry; MeOH: methanol; TFA: trifluoroacetic acid; THF: tetrahydrofuran; tlc: thin layer chromatography.

EXAMPLE 1

Preparation of Representative Aminoethanol Intermediates

A. 1-[(Cyclohexylmethyl)amino]-2-methyl-2-propanol:

Lithium perchlorate (0.29 g, 2.77 mmol) was added to a solution of isobutylene oxide (0.2 g, 2.77 mmol) in anhydrous acetonitrile (2 mL). When all the solid had dissolved, (cyclohexylmethyl)amine (0.33 mL, 2.77 mmol) was added. The mixture was stirred at room temperature (20°–22°) for 18 h. The mixture was diluted with $Et_2O$ (25 mL), washed once with saturated brine (25 mL) and dried ($Na_2SO_4$). The solvent was removed under reduced pressure to afford the desired aminoethanol derivative (385 mg, 75% yield); $^1H$ NMR ($CDCl_3$) $\delta$2.51 (s,3H), 2.48 (s,1H), 1.80–1.60 (m, 5H), 1.50–1.08 (m,6H), 1.16 (s,6H), 1.00–0.78 (dr, J=2.2 Hz,11.8 Hz, 2H).

CAUTION!

Lithium perchlorate is a strong oxidizer and explosions involving this reagent have been reported (see R. A. Silva, Chem. Eng. News 1992, 70 (51), 2. Although problems have not been experienced using the above procedure, the reaction should be conducted behind a safety shield and on a moderate scale. Practically speaking, the procedure of D. P. Getman et al. and of A. K. Ghosh et al., J. Med. Chem., 36 (1993), pages 288 and 292, respectively, is a safe and efficient substitute for the lithium perchlorate method. A general experimental procedure is as follows:

A solution of isobutylene oxide (0.7 mL, 8.32 mmol) and (cyclohexylmethyl)amine (0.72 mL, 5.54 mmol) in absolute ethanol (2.5 mL) was stirred at room temperature for 15 h. Thereafter, the solvent was removed under reduced pressure and the residue was purified by flash chromatography (SiO$_2$, eluent: EtOAc) to give the desired aminoethanol derivative as a colorless oil (641 mg, 62%).

B. 1-[(Methylamino)methyl]cyclohexanol:

Excess methylamine gas was bubbled for several minutes into a cooled solution (0°) of 1-oxaspiro[2.5]octane [2.0 g, 17.8 mmol, described by E. J. Corey and M. Chaykovsky, Org. Syn., Coll. Vol. V, 755 (1973)] in toluene (30 mL) contained in a thick-walled glass tube. The tube was evacuated, sealed and then heated at 120° behind a safety shield for 3 days. The tube was cooled and the contents removed. Volatiles were removed from the contents by evaporation under reduced pressure to give the desired aminoethanol derivative as a colorless oil (2.25 g, 96%); $^1$H NMR (CDCl$_3$) δ2.51 (s,2H), 2 46 (s,3H), 2.40–2.20 (broad m,2H), 1.72–1.22 (m,10H).

C. (R)-2-Amino-1-phenylethanol:

A 2M solution of trimethylaluminum in toluene (1.25 mL, 2.5 mmol) was added dropwise over 3 min to a solution of benzylamine (273 μL, 2.5 mmol) in anhydrous CH$_2$Cl$_2$ (7.5 mL) at room temperature. The mixture was stirred for 30 min. A solution of (R)-styrene oxide (284 μL, 2.5 mmol) in CH$_2$Cl$_2$ (3 mL) was added over three min. The resulting solution was stirred for 18 h. The aluminate was hydrolyzed by carefully adding a 6M aqueous solution of NaOH (2 mL, 12 mmol) and stirring the resulting two phase mixture vigorously for 2 h. The organic phase was separated and the aqueous phase was extracted with CH$_2$Cl$_2$ (2×10 mL). The organic material was combined, washed with saturated brine (20 mL), dried (MgSO$_4$) and the solvent was removed under reduced pressure to give a pale yellow solid (512 mg). The solid was purified by chromatography (SiO$_2$, eluent: EtOAc-hexane, 1:1) to give (117 mg, 20%) of (R)-2-[(phenylmethyl) amino]-1-phenylethanol. A mixture of the latter compound (50 mg, 0.22 mmol)and 10% (w/w) Pd(OH)$_2$/C (10 mg) in MeOH (2 mL) was exposed to H$_2$ gas (1 atmosphere) at room temperature for 3 h. The mixture was filtered and the filter washed with MeOH. The filtrate and washings were combined and evaporated under reduced pressure to give (R)-2-amino- 1-phenylethanol as a pale yellow solid (29 mg, 96%), $^1$H NMR (400 MHz, CDCl$_3$) δ7.38–7.26 (m,5H), 4.67 (dd, J=3.9 Hz,7.8 Hz,1H), 3.03 (dd, J=3.6 Hz,12.6 Hz,1H), 2.85 (dd, J=7.8 Hz,12.8 Hz,1H), 1.87 (broad s,3H). This aminoethanol was used for ensuing coupling steps without further purification.

D. 1-{[(Phenylmethyl)amino]methyl}cyclohexanol:

Benzaldehyde (1.2 mL, 10 mmol) and NaBH$_3$CN (1.51 g, 24 mmol) were added serially to a cold solution (0°) of 1-(aminomethyl)cyclohexanol hydrochloride (1.65 g, 10 mmol) in anhydrous MeOH (40 mL). After stirring for 1 h, the reaction mixture was poured into H$_2$O (100 mL) and the pH of the resulting mixture was adjusted to 11 by the addition of a 2M aqueous solution of NaOH. The mixture was extracted with Et$_2$O (3×50 mL). The combined Et$_2$O extracts were in turn extracted with a 1M aqueous solution of HCl (4×20 mL). The aqueous extract was washed once with Et$_2$O (30 mL), rendered basic (pH=10) by the addition of a 2M aqueous solution of NaOH, and extracted with Et$_2$O (3×50 mL). The combined Et$_2$O extracts were washed with brine, dried (Na$_2$SO$_4$) and evaporated to dryness under reduced pressure. The residue was purified by chromatography (SiO$_2$, eluent: EtOAc) to give the desired aminoethanol derivative (1.9 g, 89%); $^1$H NMR (CDCl$_3$) δ7.31 (s,5H), 3.83 (s,2H), 2.56 (s,2H), 1.75–1.20 (m,12H).

E. N,N-Dimethyl-2-{[(1-hydroxycyclohexyl)methyl]amino}acetamide:

A solution of 1-(aminomethyl)cyclohexanol hydrochloride (2.0 g, 12.1 mmol) in MeOH (5 mL) was cooled to 0°. 2-Bromo-N,N-dimethylacetamide (2.0 g, 12.1 mmol) was added to the solution, followed by the dropwise addition of triethylamine (2.51 mL, 34 mmol). The mixture was stirred at room temperature for 18 h, diluted with a 5% aqueous solution of NaHCO$_3$(10 mL) and brine (20 mL) and extracted with EtOAc (3×20 mL). The combined EtOAc extracts were washed with brine, dried (MgSO$_4$) and concentrated to dryness under reduced pressure. The residue was purified by chromatography (SiO$_2$, eluent: EtOH-EtOAc, 1:3) to give the desired aminoethanol derivative as a white solid (0.57 g, 22%), $^1$H NMR (DMSO-d$_6$) δ4.05 (broad s,1H), 3.33 (s,2H), 2.89 (s,3H), 2.82 (s,3H), 2.39 (s,2H), 1.60–1.10 (m,11H).

F. 1-{{[(3,4-Methylenedioxyphenyl)methyl]amino}methyl}cyclohexanol:

This compound was prepared by a procedure analogous to that of section A; $^1$H NMR (CDCl$_3$) δ6.85 (s,1H), 6.76 (s,2H), 5.94 (s,2H), 3.76 (s,2H), 2.55 (s,2H), 2.40–2.10 (broad m,2H), 1.77–1.20 (m,10H).

G. 1-{[(3-Pyridinylmethyl)]amino]methyl}cyclohexanol:

This compound was prepared by a procedure analogous to that of section D. It was purified as its Boc derivative (Boc$_2$O,NaOH,THF-H$_2$O); $^1$H NMR (400 MHz, CDCl$_3$) δ8.50 (t,2H), 7.66–7.50 (m, 1H), 7.30–7.26 (m, 1H), 4.72–4.50 (m,2H), 3.33–3.12 (m,2H), 1.65–1.14 (m,11H), 1.40 (s,9H). The Boc derivative was deprotected (5M HCl/ 1,4-dioxane) to give the desired aminoethanol derivative which was used for an ensuing coupling step.

H. 1-}}[2-(2-Pyridinyl)ethyl]amino}methyl}cyclohexanol:

This compound was prepared by a procedure analogous to that of section A. It was purified as its Boc derivative (Boc$_2$O,NaOH,THF-H$_2$O), $^1$H NMR (CDCl$_3$) δ8.52 (d, J=4.4Hz,1H), 7.64 (t, J=7.3 Hz,1H), 7.25–7.10 (m,2H), 4.45–4.05 (broad s,1H), 3.65 (t, J=7.3 Hz,2H), 3.17 (s,2H), 3.03 (t, J=7.3 Hz,2H), 1.75–1.10 (m,10H), 1.40 (s,9H). The Boc derivative was deprotected (5M HCl/1,4-dioxane) to give the desired aminoethanol derivative which was used for an ensuing coupling step.

I. 1-}[(2-hydroxyethyl)amino]methyl}cyclohexanol:

This compound was prepared by a procedure analogous to that of section A. It was purified as its Boc derivative (Boc$_2$O,NaOH,THF-H$_2$O); $^1$H NMR (DMSO-d$_6$) δ4.55–4.10 (broad s,2H), 3.50 (t,2H), 3.44 (t,2H), 3.16 (s,2H), 1.60–1.13 (m,10H), 1.36 (s,9H). The Boc derivative was deprotected (5M HCl/1,4-dioxane) to give the desired aminoethanol derivative which was used for an ensuing coupling step.

J. 2-{[(1-Hydroxycycloheptyl)methyl]amino}-N-methyl-N-[2-(2-pyridinyl)ethyl]acetamide:

This compound was prepared by a procedure analogous to that of section A using 2-amino-N-methyl-N-[2-(2-pyridinylethyl]acetamide and 1-oxospira[2.6]nonane (prepared by the procedure of Corey and Chaykovsky noted in section B) as starting materials. The $^1$H NMR(DMSO-d$_6$) of the compound showed δ8.49 (t, J=4.8 Hz, 1H), 7.75–7.65 (m,1H), 7.31–7.18 (m,2H), 4.37 (t, J=5.1 Hz, 1H), 4.05 (d, J=8.8 Hz, 1H), 3.65–3.56 (m,2H), 3.50–3.31 (m,2H), 2.96–2.88 (m,2H), 2.85 and 2.82 (s,3H), 1.95–1.80 (broad m,1H), 1.45–0.95 (m,13H).

K. 2-{[(1-Methoxycyclohexyl)methyl]amino}-N-methyl-N-[an example of alkoxyalkylamine of formula ANH(R$^1$)]:

A solution of benzyl bromoacetate (0.49 mL, 3.1 mmol) in THF (6.4 mL) was cooled to 0°. Triethylamine (0.54 mL, 3.9 mmol) and 1-methoxycyclohexanemethanamine (0.37 g, 2.58 mmol), described by N. J. Leonard and K. Jann, J. Am. Chem. Soc., 84, 4806 (1962), were added to the cooled solution. The mixture was stirred at room temperature for 24 h. Thereafter, H$_2$O (1.6 mL) was added, followed by the addition of a saturated aqueous solution of NaHCO$_3$ (3.22 mL) and di-tert-butyl dicarbonate (0.79 g, 3.61 mmol). The resulting mixture was stirred vigorously for 24 h. Thereafter, the mixture was diluted with H$_2$O (25 mL) and extracted with EtOAc (3×). The combined extracts were washed with brine, dried (Na$_2$SO$_4$) and concentrated to dryness to afford 2-{tert-butyloxycarbonyl[(1-methoxycyclohexyl)methyl]amino}acetic acid benzyl ester (1.25 g).

The latter ester (1.25 g) was dissolved in THF/H$_2$O (3:2,25 mL). After LiOH (0.30 g, 12.9 mol) was added, the mixture was stirred at room temperature for 20 h. The mixture was concentrated under reduced pressure. H$_2$O (13 mL) was added to the residue. The resulting solution was washed with EtOAc, rendered acidic by the addition of aqueous 1M HCl and extracted with EtOAc (3×). The combined EtOAc extracts were washed with brine, dried (Na$_2$SO$_4$) and concentrated to dryness to give the acetic acid propanoic acid methyl ester [32.58 g, 0.21 mol, described by J. Altman et al., J. Chem. Soc., Perkin Trans. 1, 59 (1984)] and triphenylmethyl chloride (64.80 g, 0.23 mmol) in CH$_2$Cl$_2$ at room temperature. The mixture was stirred at room temperature for 63 h, diluted with CH$_2$Cl$_2$ (total volume=900 mL), washed with H$_2$O (2×), a saturated aqueous solution of NaHCO$_3$ (1×) and brine (1×), dried (MgSO$_4$) and concentrated to dryness under reduced pressure. The residue was dissolved in a mixture of THF/H$_2$O (630 mL: 210 mL). Lithium hydroxide monohydrate (22.03 g, 0.52 mol) was added to the solution. The mixture was stirred at room temperature for 3 h. Most of the THF was removed by distillation under reduced pressure. The residue was poured into H$_2$O (1 L). The pH of the resulting mixture was adjusted to 2 by the addition of 10% (w/v) aqueous citric acid. The mixture was extracted with CH$_2$Cl$_2$(3×). The CH$_2$Cl$_2$ extract was washed with 10% (w/v) aqueous citric acid and brine, dried (MgSO$_4$) and concentrated under reduced pressure. The residue was triturated with Et$_2$O to give the desired acid as a white solid (77.14 g, 96%); $^1$H NMR (CDCl$_3$) δ7.67 (d, J=1.5 Hz,1H), 7.41–7.34 (m,9H), 7.13–7.08 (m,6H), 6.66 (d, J=1.5 Hz,1H), 2.95–2.88 (m,2H), 2.82–2.76 (m,2H).

(b) 4(S)-(1-Methylethyl)-3-{1-oxo-3-[1-(triphenylmethyl)-1H-imidazol-4-yl]propyl}-2-oxazolidinone:

By following the procedure of this example, section A(a), and using the preceding product (11.5 g, 30.1 mmol) to prepare the corresponding mixed anhydride which in turn is reacted with the (S)-4-(1-methylethyl)- 2-oxazolidinone (3.53 g, 27.3 mmol), the desired product was obtained as a pale yellow solid (11.38 g, 84%); $^1$H NMR (CDCl$_3$) δ7.36–7.29 (m,10H), 7.17–7.10 (m,6H), 6.58 (d, J=0.7Hz, 1H), cyclohexanecarboxaldehyde (2.42 mL, 20 mmol). The mixture was allowed to come to room temperature and then stirred for 2 h. THF (40 mL), a saturated aqueous solution of NaHCO$_3$ (30 mL) and di-tert-butyl dicarbonate (4.36 g, 20 mmol) were added serially to the mixture. The mixture was stirred vigorously for 2 h. Thereafter, the mixture was diluted with EtOAc. The organic phase was separated, washed with H$_2$O (3×) and brine (1×), dried (Na$_2$SO$_4$) and concentrated to dryness under reduced pressure. The oily residue was purified by chromatography (SiO$_2$, eluent: EtOAc-hexane, 1:3) to give 2-[N-tert-butyloxycarbonyl-N-(cyclohexylmethyl)amino]acetic acid methyl ester as a colorless oil (4.56 g, 80%); $^1$H NMR(CDCl$_3$) (approximately a 1:1 mixture of rotamers) δ3.94 (s,1H), 3.85 (s,1H), 3.725 and 3.721 (s,3H), 3.09 (dd, J=6.2 Hz,7.1 Hz, 2H), 1.75–1.55 (broad m,6H), 1.46 and 1.41 (s,9H), 1.40–1.05 (m,3H), 1.02–0.75 (broad m,2H).

(b) A solution of the latter compound (1.43 g, 5 mmol) in toluene (30 mL) was cooled to −78°. A 1.5M solution of diisobutyl aluminum hydride in toluene (3.7 mL, 5.5 mmol) was added over 5 min to the cooled solution. After being stirred at the same temperature for 1.5 h, the reaction mixture was quenched by the addition of a few drops of MeOH followed by the addition of a saturated aqueous solution of NH$_4$Cl. The mixture was allowed to come to room temperature and then diluted with H$_2$O (50 mL). The organic layer was decanted and the aqueous layer was extracted with EtOAc (3×). The combined organic phases were washed with brine (1×), dried (Na$_2$SO$_4$) and concentrated to dryness under reduced pressure to give 2-[N-tert-butyloxycarbonyl-N-(cyclohexylmethyl)amino]acetaldehyde as a colorless oil (1.29 g).

(c) A solution of the latter compound (1.29 g) in anhydrous THF (30 mL) was cooled to −20°. A 2M solution of isopropyl magnesium chloride in Et$_2$O (7.5 mL, 15 mmol of reagent) was added to the cooled solution. The mixture was stirred at −20° for 1.5 h and then quenched by the addition of a saturated aqueous solution of NH$_4$Cl (15 mL) and H$_2$O (100 mL). The mixture was extracted with EtOAc (4×). The extract was washed with saturated brine (1×), dried (Na$_2$SO$_4$) and concentrated under reduced pressure to give the corresponding secondary alcohol of the desired aminoketone as a colorless oil (1.30 g). The oil was dissolved in anhydrous CH$_2$Cl$_2$ (50 mL). Powdered molecular sieves (4A, 2 g), N-methylmorpholine N-oxide (879 mg, 7.5 mmol) and tetrapropylammonium perruthenate (88 mg, 0.25 mmol) were added successively to the solution. The mixture was stirred for 3 h and then filtered through a pad of diatomaceous earth. The filtrate was concentrated to dryness under reduced pressure. The residue was dissolved in EtOAc. The solution was washed with brine (1×), dried (Na$_2$SO$_4$) and concentrated to dryness under reduced pressure. The black residue was purified by chromatography (SiO$_2$, eluent: EtOAc-hexane, 3:22) to give the Boc derivative of the desired aminoketone as a colorless oil [441 mg, 29% from the methyl ester of step (a) of this procedure]; $^1$H NMR(CDCl$_3$) (approximately a 1:1 mixture of rotamers) δ4.05 (s,1H), 3.96 (s,1H), 3.05 (dd, J=9.1 Hz,7.3 Hz, 2 H), 2.63 (hept, J=8.0 Hz, 1H), 1.80–1.56 (broad m,6H), 1.45 and 1.39 (s,9H), 1.30–0.85 (m,5H), 1.12 (d, J=7.0 Hz, 3H), 1.11 (d, J=7.0 Hz, 3H). The Boc derivative was deprotected in the usual manner to give the desired aminoketone which was used for an ensuing coupling step.

EXAMPLE 2

Preparation of Representative Amido acids of
Formula HO—C(O)CH$_2$CH(R$^2$)C(O)—B (Formula 4)

A. 3(R)-(Cyclopropylmethyl)-4-{[1(S)-(cyclohexylmethyl)- 2(R), 3(S)-dihydroxy-5-methylhexyl ]amino}-4-oxobutanoic Acid (a) 3-(3-Cyclopropyl-1-oxopropyl)-4(S)-(1-methylethyl)-2-oxazolidinone:

A solution of mixed anhydride was prepared by adding under a N$_2$ atmosphere pivaloyl chloride (14.8 mL, 120 mmol) over a period of 5 min to a cooled solution (0°) of 4-pentenoic acid (12.3 mL, 120 mmol) and N-methylmorpholine (15.4 mL, 140 mmol). The mixture was stirred at 0° for 30 min. Meanwhile, a second solution was prepared by adding dropwise under a N$_2$ atmosphere a 1.4M solution of butyllithium in hexane (71 mL, 100 mmol) to a stirred cooled solution (−78°) of (S)-4-(1-methylethyl)-2-oxazolidinone [12.9 g, 100 mmol, described by L. N. Pridgen et al., J. Org. Chem., 54, 3231 (1989)] in dry THF (300 mL) over a period of 45 min. (Note: The agitation was done by an overhead stirrer.) After stirring for 15 min at −78°, the latter solution was added by cannulation to the stirred solution of the mixed anhydride at −78° over a period of 20 min. The mixture was stirred for an additional 30 min at the same temperature. A saturated aqueous solution of NH$_4$Cl (50 mL) was added and the mixture was allowed to warm to room temperature. The mixture was diluted with H$_2$O (300 mL). The organic layer was separated. The aqueous layer was extracted with EtOAc (3×). The combined organic phases were dried (Na$_2$SO$_4$) and evaporated to dryness under reduced pressure to give an oily residue [i.e. 4(S)-(1-methylethyl)-3-(1-oxo-4-pentenyl)-2-oxazolidinone].

The latter oil was dissolved in 175 mL of a 0.4M Et$_2$O solution of diazomethane. The resulting solution was cooled to 0°. Palladium(II) acetate (112 mg, 0.5 mmol) was added to the cooled solution. The solution bubbled vigorously. After the bubbling subsided, additional palladium(II)acetate (112 mg, 0.5 mmol) and the Et$_2$O solution of diazomethane (175 mL) were added and the ensuing bubbling was allowed to subside. The latter addition was repeated two more times. (The total amount of diazomethane solution added was 700 mL.) The mixture was filtered through diatomaceous earth. The filtrate was concentrated under reduced pressure. The residual oil was purified by chromatography (SiO$_2$, eluent: EtOAc-hexane, 1:4) followed by distillation (100° at 0.05 mm Hg) to give the desired N-(3-cyclopropyl- 1-oxopropyl)-2-oxazolidinone derivative (20.0 g, 89%), $^1$H NMR (CDCl$_3$) δ4.41 (complex m,1H), 4.28 (d, J =9.1 Hz, 1H), 4.20 (dd, J=3.4 Hz,8.8 Hz, 1H), 3.05 (m,2H), 2.36 (m,1H), 1.55 (q, J=7.3 Hz, 2H), 0.91 (d, J=7.2 Hz, 3H), 0.87 (d, J=7.1 Hz, 3H), 0.89 (m,1H), 0.43 (m,2H), 0.08 (m,2H).

(b) 3-[4-tert-Butoxy-1, 4-dioxo-2(R)-(cyclopropylmethyl) butyl]-4(S)-(1-methylethyl)-2-oxazolidinone:

A 1.4M solution of butyllithium in hexane (70.0 mL, 97.6 mmol) was added over a period of 20 min to a cooled solution (0 °) of diisopropylamine (15.0 mL, 106 mmol) in dry THF (150 mL). After stirring at 0° for 15 min, the solution was cooled to −78°. A solution of the previously noted N-(3-cyclopropyl-1-oxopropyl)- 2-oxazolidinone (20.0 g, 88.8 mmol) in THF (40 mL) was added to the cooled solution over 45 min. The mixture was stirred for 1 h at −78°. 1;3-Dimethyl- 3,4,5,6-tetrahydro-2(1H)-pyrimidinone (23.6 mL, 195 mmol) was added to the mixture, followed by the addition of a solution of tert-butyl 2-bromoacetate (15.1 mL, 93.2 mmol) in THF (20 mL) over a 10 min period. Thereafter, the mixture was stirred for 1.5 h at −78°. The reaction mixture was quenched with a saturated aqueous solution of NH$_4$Cl and then allowed to warm to room temperature. The mixture was diluted with EtOAc (250 mL). The organic layer was separated, washed with 5% (w/v) aqueous citric acid (3×), a saturated aqueous solution of NaHCO$_3$ (2×) and brine, dried (Na$_2$SO$_4$) and concentrated to dryness under reduced pressure. The residual oil was crystallized from EtOAc/hexane to give the desired oxazolidinone derivative as colorless crystals (21.7 g, 72%); mp 104°–105°; [α]$_D^{23}$+52.8° (c 1.02, CHCl$_3$).

(c) 3(R)-(Cyclopropylmethyl)-4-{[1(S)-(cyclohexylmethyl)-2(R),3(S)-dihydroxy-5-methylhexyl]amino}butanoic Acid tert-Butyl Ester:

A solution of the latter oxazolidinone derivative (10.2 g, 30 mmol) in THF/H$_2$O (150 mL / 20 mL) was cooled to 0°. A 30% aqueous solution of H$_2$O$_2$ (9.5 mL, 90 mmol of H$_2$O$_2$) was added to the cooled solution. Thereafter, an aqueous 1M solution of LiOH (30 mL, 30 mmol of LiOH) was added dropwise at 0° over a 5 min period. The mixture was allowed to warm to room temperature. After being stirred at room temperature for 3 h, the mixture was cooled to 0° and an aqueous 1M solution of Na$_2$SO$_3$ (135 mL, 135 mmol) was added over a period of 10 min. After another 10 min of stirring, the mixture was diluted with H$_2$O and washed with chloroform (3×). The aqueous layer was rendered acidic (pH 4) by the addition of solid citric acid and extracted with EtOAc (3×). The combined EtOAc extracts were washed with brine, dried (Na$_2$SO$_4$) and concentrated to dryness to give the desired monoprotected dicarboxylic acid, i.e. the 4-tert-butyl ester of 2(R)-(cyclopropylmethyl)butanedioic acid, as a colorless oil (6.65 g, 97%); [α]$_D^{23}$+16.1° (c 2.61, CHCl$_3$). The monoprotected dicarboxylic acid was used for the following coupling step without purification.

2 (S)-(tert-Butoxycarbonyl)amino-1-cyclohexyl-6-methyl- 3(R),4(S)-heptanediol (3.61 g, 10.5 mmol) was dissolved in a 5N solution of HCl in 1,4-dioxane (15 mL). The solution was stirred at room temperature for 2 h. The solvent and excess HCl were removed from the solution under reduced pressure and the resulting hydrochloric acid addition salt was dried under reduced pressure for 18 h. Thereafter, the hydrochloric acid addition salt was dissolved in anhydrous DMF (20 mL) and the solution was cooled to 0°. N-Methylmorpholine (6.3 g, 63 mmol), a solution of the preceding monoprotected dicarboxylic acid (2.39 g, 10.5 mmol) in anhydrous DMF (5 mL) and BOP•PF$_6$ (4.86 g, 11.0 mmol) were added to the cooled solution. After the mixture had been allowed to warm to room temperature, it was stirred at that temperature for 1.5 h. The mixture was diluted with EtOAc (100 mL). The organic phase was washed with a 5% (w/v) aqueous solution of citric acid (3×), a saturated solution of NaHCO$_3$ (2×) and brine (1×), dried (Na$_2$SO$_4$) and concentrated under reduced pressure to give the desired compound, i.e. the protected amido acid of formula 3 in which W$^1$ is tert-butoxy, R$^2$ is cyclopropylmethyl and B is 1(S)-(cyclohexylmethyl)-2(R), 3(S)-dihydroxy-5-methylhexylamino, as a white crystalline material (3.74 g, 78%) after crystallization from EtOAc-hexane; mp 138°–139°; $^1$H NMR (CDCl$_3$) δ5.87 (d, J=8.9 Hz, 1H), 4.41 (broad s, 1H), 4.32 (dr, J=4.4 Hz,9.1 Hz, 1H), 3.22 (broad s,2H), 2.68–2.39 (m,2H), 2.00–1.10 (complex m, 22H), 1.44 (s, 9H), 0.93 (d, J=6.7 Hz, 3H), 0.83 (d, J=6.5 Hz, 3H), 0.75–0.65 (m,1H), 0.48 (m,2H), 0.08 (broad m,1H).

(d) 3(R)-(Cyclopropylmethyl)-4-{[(S)-(cyclohexylethyl)-2(R),3(S)-dihydroxy-5-methylhexyl]amino}-4-oxobutanoic Acid:

The product of previous section (c) (329 mg, 0.72 mmol) was deprotected in a solution of TFA (1.2 mL) in anhydrous $CH_2Cl_2$ (2.4 mL), which was allowed to stand at 0° for 10 min and then at room temperature for 1.5 h, to give (after evaporation of the volatiles under reduced pressure) a crude product (369 mg). The crude product was triturated several times with $Et_2O$ to give the desired amido acid of formula 4 wherein $R^2$ is (cyclopropylmethyl) and B is 1(S)-(cyclohexylmethyl)-2(R),3(S)-dihydroxy-5-methylhexylamino as a white solid (193 mg, 67%). The compound was used without further purification for ensuing coupling steps.

B. Preparation of 4-{[1(S)-(Cyclohexylmethyl)2(R),3(S)-dihydroxy-5-methylhexyl]amino}-4-oxo-3-(R){[1-(triphenylmethyl)-1H-imidazol-4-yl]methyl}butanoic acid (a) 1-(Triphenylmethyl)-1H-imidazole-4-propanoic Acid:

Triethylamine (26.73 g, 36.8 mL, 0.26 mol) was added dropwise to a solution of 1H-imidazole-4-propanoic acid methyl ester [32.58 g, 0.21 mol, described by J. Altman et al., J. Chem. Soc., Perkin Trans. 1, 59 (1984)] and triphenylmethyl chloride (64.80 g, 0.23 mmol) in $CH_2Cl_2$ at room temperature. The mixture was stirred at room temperature for 63 h, diluted with $CH_2Cl_2$ (total volume=900 mL), washed with $H_2O$ (2×), a saturated aqueous solution of $NaHCO_3$ (1×) and brine (1×), dried ($MgSO_4$) and concentrated to dryness under reduced pressure. The residue was dissolved in a mixture of THF/$H_2O$ (630 mL: 210 mL). Lithium hydroxide monohydrate (22.03 g, 0.52 mol) was added to the solution. The mixture was stirred at room temperature for 3 h. Most of the THF was removed by distillation under reduced pressure. The residue was poured into $H_2O$ (1 L). The pH of the resulting mixture was adjusted to 2 by the addition of 10% (w/v) aqueous citric acid. The mixture was extracted with $CH_2Cl_2$ (3×). The $CH_2Cl_2$ extract was washed with 10% (w/v) aqueous citric acid and brine, dried ($MgSO_4$) and concentrated under reduced pressure. The residue was triturated with $Et_2O$ to give the desired acid as a white solid (77.14 g, 96%); $^1H$ NMR ($CDCl_3$) δ7.67 (d, J=1.5 Hz, 1H), 7.41–7.34 (m,9H), 7.13–7.08 (m,6H), 6.66 (d, J=1.5 Hz, 1H), 2.95–2.88 (m,2H), 2.82–2.76 (m,2H).

(b) 4(S)-(1-Methylethyl)-3-{1-oxo-3-[1-(triphenylmethyl)-1H-imidazol-4-yl]propyl}-2-oxazolidinone:

By following the procedure of this example, section A(a), and using the preceding product (11.5 g, 30.1 mmol) to prepare the corresponding mixed anhydride which in turn is reacted with the (S)-4-(1-methylethyl)-2-oxazolidinone (3.53 g, 27.3 mmol), the desired product was obtained as a pale yellow solid (11.38 g, 84%); $^1H$ NMR ($CDCl_3$) δ7.36–7.29 (m,10H), 7.17–7.10 (m,6H), 6.58 (d, J=0.7 Hz, 1H), 4.40 (td, J=3.8 Hz, 7.5 Hz,1H), 4.29–4.14 m,2H), 3.32–3.23 (m,2H), 2.96–2.88 (m,2H), 2.33 (hept d, J=3.8 Hz, 6.9 Hz, 1H), 0.89 (d, J=7.0 Hz, 3H), 0.82 (d, J=6.9 Hz, 3H).

(c) 3-{1,4-Dioxo-4-(phenylmethoxy)-2(R)-{[1-triphenylmethyl)-1H-imidazol-4-yl]methyl}butyl}-4(S)-(1-methylethyl)-2-oxazolidinone:

A 1.0M solution of sodium bis (trimethylsilyl)amide (18.0 mL, 18.0 mmol, Aldrich Chemical Co., Inc., Milwaukee, Wis., U.S.A.) was added dropwise (18 min) to a cold (−78°) solution of the product of the preceding section (8.06 g, 16.3 mmol) in THF (65 mL). After 40 min at −78°, a solution of benzyl 2-bromoacetate (7.48 g, 32.7 mmol) in THF (2 mL) was added dropwise to the solution. The reaction mixture was stirred at for 1.5 h, quenched with an aqueous saturated solution of $NH_4Cl$, allowed to warm to room temperature and then poured into a mixture of $H_2O$ (500 mL) and aqueous saturated solution of $NH_4Cl$ (100 mL). The resulting mixture was extracted with EtOAc. The EtOAc extract was washed with a saturated aqueous solution of $NaHCO_3$ and then brine, dried ($MgSO_4$) and concentrated under reduced pressure to give 3-{1,4-dioxo-4-(phenylmethoxy)-2-{[1-(triphenylmethyl)-1H-imidazol-4-yl]methyl}butyl}-4(S)-(1-methylethyl)-2-oxazolidinone as a mixture of 2(R)- and 2(S)-epimers in a 8 to 1 ratio by weight. Separation of the epimers by flash chromatography ($SiO_2$, eluent: hexane-EtOAc, 1:2) yielded the desired 2(R)-epimer (Rf=0.25, eluent: hexane-EtOAc,1:2). The $^1H$ NMR ($CDCl_3$) of the 2(R)-epimer showed δ7.34–7.28 (m, 15H), 7.13–7.08 (m,6H), 6.59 (d, J=1.3 Hz, 1H), 5.06 (s,2H), 4.55–4.45 (m,1H), 4.38 (td, J=3.9 Hz,5.4 Hz, 1H), 4.15–4.10 (m,2H), 2.97 (dd, J=10.3 Hz,16.9 Hz, 1H), 2.88 (dd, J=6.3 Hz,14.3 Hz, 1H), 2.73 (dd, J=7.0 Hz,14.3 Hz, 1H), 2.59 (dd, J=4.4 Hz,16.9 Hz, 1H), 2.32 (hept d, J=3.9 Hz,7.0 Hz, 1H), 0.87 (d, J=7.1 Hz, 3H), 0.85 (d, J=6.8 Hz, 3H).

(d) 4-{[1(S)-(Cyclohexylmethyl)-2(R),3(S)-dihydroxy-5-methylhexyl]amino}-4-oxo-3(R)-{[(1-(triphenylmethyl)-1H-imidazol-4-yl]methyl}butanoic Acid Benzyl Ester:

A 30% aqueous solution of $H_2O_2$ (4.70 mL, 41.6 mmol) and lithium hydroxide monohydrate (436 mg, 10.4 mmol) were added serially to cooled solution (0°) of the product of preceding section (c) (6.67 g, 10.4 mmol) in THF/$H_2O$ (156 mL: 52 mL). The reaction mixture was stirred at 0° for 2 h and then at room temperature for 2 h. Excess peroxide was quenched at 0° with 1.5N aqueous $Na_2SO_3$ solution. THF was removed by distillation under reduced pressure. The concentrate was poured into $H_2O$ (500 mL). The mixture was rendered acid by the addition of a 10% (w/v) aqueous solution of citric acid, and then extracted with EtOAc. The extract was washed with brine, dried ($MgSO_4$) and evaporated to dryness under reduced pressure to yield the desired monoprotected dicarboxylic acid, i.e. the 4-(phenylmethyl) ester of 2(R)-{[1-(triphenylmethyl)-1H-imidazol-4-yl]methyl}butanedioic acid. The monoprotected dicarboxylic acid was used for the following coupling step without further purification.

2(S)-Amino-1-cyclohexyl-6-methyl-3(R),4(S)-heptanediol hydrochloride (2.91 g, 10.4 mmol), DIPEA (3.62 g, 28.0 mmol) and BOP•$PF_6$ (4.82 g, 10.9 mmol) were added to a cooled (0°) solution of the preceding monoprotected dicarboxylic acid in DMF (42 mL). The mixture was stirred at room temperature for 6 h. Thereafter, the mixture was diluted with EtOAc. The organic phase was washed with a 10% (w/v) aqueous solution of citric acid (2×), $H_2O$ (1×), a saturated aqueous solution of $NaHCO_3$ and brine, dried ($MgSO_4$) and concentrated to dryness under reduced pressure. The residue was purified by flash chromatography ($SiO_2$, eluent: hexaneisopropanol,8:1) to give the desired protected amido acid as a white solid (6.08 g, 77%); $^1H$ NMR ($CDCl_3$) δ7.42 (d, J=1.2 Hz, 1H), 7.37–7.30 (m,14H), 7.12–7.05 (m,6H), 6.54 (d, J=1.2 Hz, 1H), 6.45 (broad d, J=9.6 Hz, 1H), 5.11 (d, J=12.3 Hz, 1H), 5.06 (d, J=12.3 Hz,1H), 4.43–4.38 (m,1H), 3.30–2.64 (m,6H), 2.37 (dd, J=4.8 Hz,15.6 Hz, 1H), 1.92–0.73 (m, 16H), 0.87 (d, J=6.6 Hz, 3H), 0.69 (d, J=6.5 Hz, 3H).

(e) $N^1$-[1(S)-(Cyclohexylmethyl)-2(R),3(S)-dihydroxy-5-methylhexyl]-$N^4$-[2-(dimethylamino)-2-oxoethyl]-$N^4$-[1(S)-phenylethyl]-2(R)-{[1-(triphenylmethyl)-1H-imidazol-4-yl]methyl}butanediamide:

A mixture of the protected amido acid of the previous section (d) (6.08 g, 8.04 mmol) and 10% palladium on carbon (600 mg) in EtOH (80 mL) was stirred under one atmosphere of hydrogen for 2.5 h. The mixture was filtered and the filtrate was concentrated to dryness under reduced pressure to give 4-{[1(S)-(cyclohexylmethyl)- 2(R),3(S)- dihydroxy-5-methylhexyl]amino}3(R)-{[1-(triphenylmethyl)-1H-imidazol-4-yl]methyl}4-oxobutanoic acid, i.e. the amido acid of formula 4 in which $R^2$ is {[1-(triphenylmethyl)-1H-imidazol-4-yl]methyl} and B is 1(S)-(cyclohexylmethyl)2(R),3(S)-dihydroxy-5-methylhexylamino, as a white solid (5.30 g, 99%). The amido acid was used for ensuing coupling steps without further purification.

C. Preparation of 4-{[1(S)-(Cyclohexylmethyl)2(R),3(S)-dihydroxy-5-methylhexyl]amino}-4-oxo-3(R)-{{2-[(2,2,2-trichloroethoxy)carbonylamino]-4-thiazolyl}methyl}butanoic Acid (a) 4-Bromo-4-pentenoic Acid:

tert-Butyl acetate (35 g, 301 mmol) was added dropwise to a stirred freshly prepared solution of lithium diisopropylamine (319 mmol) in THF (800 mL)at −78°. The mixture was stirred for 25 min at −78°. Thereafter, 2,3-dibromo-1-propene (88.6 g, 443 mmol) was added to the mixture. Stirring was continued at −78 ° for an additional 4 h. The mixture was quenched at −78° with a saturated aqueous solution of $NH_4Cl$. The THF was removed under reduced pressure. The oily residue was dissolved in EtOAc. The organic layer was washed with a saturated aqueous solution of $NH_4Cl$ (1×), $H_2O$ (1×) and brine (2×), dried ($MgSO_4$)and concentrated. The residue was dissolved in a solution of $TFA-CH_2Cl_2$ (1:1, 500 mL) and the resulting solution was allowed to stand at room temperature for 1 h. The volatiles were removed by evaporation under reduced pressure. The residue was taken up in a saturated aqueous solution of $NaHCO_3$. The resulting solution was washed twice with $CH_2Cl_2$. The aqueous phase was rendered acidic with 1N aqueous HCl and extracted with EtOAc (2×). The EtOAc extract was washed with brine (1×), dried ($MgSO_4$) and evaporated to dryness to give 4-bromo-4-pentenoic acid (39.7 g, 74 %); $^1H$ NMR ($CDCl_3$) δ11.45 (broad s,1H), 6.13 (d, J=2.9 Hz, 1H), 5.93 (d, J=2.9 Hz, 1H), 3.40–3.05 (m,4H).

(b) 3-(4-Bromo-1-oxo-4-pentenyl)-4(S)-(1-methylethyl)-2-oxazolidinone:

A solution of mixed anhydride was prepared by adding under a $N_2$ atmosphere pivaloyl chloride (253 μL, 2.06 mmol) to a stirred solution of 4-bromo-4-pentenoic acid of the previous section (350 mg, 1.96 mmol) and triethylamine (332 μL, 2.38 mmol) in dry THF (3.3 mL) cooled to −78°. The mixture was warmed to 0°, stirred for 1 h and then cooled to −78°. Another solution was prepared by adding dropwise under a $N_2$ atmosphere a 1.6M hexane solution of butyllithium (1.1 mL, 1.79 mmol) to a cooled solution (−45° to −50°) of (S)-4-(1-methylethyl)- 2-oxazolidinone [230 mg, 1.79 mmol, described by L. N. Pridgen et al., J. Org. Chem., 54, 3231 (1989)] in dry THF (8.9 mL). The latter solution was cooled to −78° and then added rapidly, via cannulation, to the stirred solution of the mixed anhydride, noted previously. The resulting mixture was stirred at −78° for 2 h. After warming to 0°, the mixture was partitioned between $CH_2Cl_2$ and phosphate buffer (pH 7). The $CH_2Cl_2$ layer was separated, washed with a saturated aqueous solution of $NaHCO_3$ (1×) and brine (1×), dried ($MgSO_4$) and evaporated to dryness under reduced pressure. The residual oil was purified by flash chromatography ($SiO_2$, eluent: EtOAc-hexane, 1:9) to give the desired 2-oxazolidinone derivative as a colorless oil (354 mg, 69%), $^1H$ NMR ($CDCl_3$) δ5.67 (d, J=2.9 Hz, 1H), 5.54 (d, J=2.9 Hz, 1H), 4.50–4.35 (m,1H), 4.35–4.15 (m,2H), 3.35–3.05 (m,2H), 2.90–2.70 (m,2H), 2.50 (hept d, J=3.8 Hz,8.6 Hz, 1H), 0.93 (d, J=8.6 Hz, 3H), 0.87 (d, J=8.6 Hz, 3H).

(c) 3-15-Bromo-1,4-dioxopentyl]-4(S)-(1-methylethyl)-2-oxazolidinone:

Recrystallized N-bromosuccinimide (960 mg, 5.39 mmol) was added to a cold (0°) stirred solution of the 2-oxazolidinone derivative of preceding section (b) (311.6 mg, 1.08 mmol) in acetonitrile (10 mL) and $H_2O$ (485 μl, 27.0 mmol). The resulting orange mixture was stirred at 0° for 30 min and then allowed to warm to room temperature. After 1 h the reaction mixture was quenched with a 10% (w/v) aqueous solution of $Na_2S_2O_3$ and extracted with EtOAc. The EtOAc extract was washed serially with $H_2O$, 10% (w/v) aqueous $Na_2S_2O_3$, $H_2O$ and brine. Drying ($MgSO_4$) and concentration of the extract afforded a yellow oil. The oil was purified by flash chromatography ($SiO_2$, eluent: EtOAc-hexane, 3:7) to give the bromoketone, 3-(5-bromo-1,4-dioxopentyl)-4(S)-(1-methylethyl)-2-oxazolidinone, as a colorless oil (320 mg, 97%); $^1H$ NMR ($CDCl_3$) δ4.50–4.35 (m,1H), 4.35–4.15 (m,2H), 4.01 (s,2H), 3.35–3.20 (m,2H), 3.05–2.90 (m,2H), 2.33 (hept d, J=3.7 Hz,7.0 Hz, 1H), 0.91 (d, J=7.0 Hz, 3H), 0.87 (d, J=7.0 Hz, 3H).

(d) 3-[3-(2-Amino-4-thiazoyl)-1-oxopropyl]-4(S)-(1-methylethyl)-2-oxazolidinone:

Thiourea (312 mg, 4.10 mmol) was added to a solution of the bromoketone of the preceding section (c) (250 mg, 0.82 mmol) in isopropanol (8.2 mL). The mixture was stirred at 50° for 20 min, cooled and evaporated to dryness under reduced pressure. The residue was dissolved in EtOAc. The EtOAc solution was washed with an saturated aqueous solution of $NaHCO_3$ (2×), $H_2O$ (2×)and brine (1×), dried ($MgSO_4$) and evaporated to dryness to give the desired aminothiazolyl derivative as a solid (197 mg, 85%); $^1H$ NMR ($CDCl_3$) δ6.16 (s,1H), 5.37 (broad s,2H), 4.55–4.35 (m,1H), 4.35–4.15 (m,2H), 3.45–3.10 (m,2H), 3.05–2.80 (m,2H), 2.35 (hept d, J=3.8 Hz,7.0 Hz, 1H), 0.90 (d, J=7.0 Hz, 3H), 0.85 (d, J=7.0 Hz, 3H). The product was used for the next step without further purification.

(e) 4(S)-(1-Methylethyl)-3-{3-{2-[(2,2,2-trichloroethoxy)carbonylamino]-4-thiazolyl}-1-oxopropyl}-2-oxazolidinone:

2,2,2-Trichloroethyl chloroformate (171 μL, 1.24 mmol) was added to a solution of the aminothiazolyl derivative of previous section (d) (185 mg, 0.65 mmol), DIPEA (205 μL, 1.18 mmol) and DMAP (8 mg, 0.07 mmol)in $CH_2Cl_2$ (3.3 mL) at room temperature. The reaction mixture was stirred at room temperature for 1 h. Thereafter, the mixture was diluted with EtOAc, washed serially with a saturated aqueous solution of $NaHCO_3$ (2×), $H_2O$ (3×) and brine (2×), dried ($MgSO_4$) and evaporated to dryness. The residue was purified by flash chromatography ($SiO_2$, eluent: EtOAc-hexane, 3:7) to give the desired product (250 mg, 84%); $^1H$ NMR (400 MHz, $CDCl_3$) δ10.27 (broad s,1H), 6.64 (s,1H), 4.93 ($q_{AB}$ $J_{AB}$=12.0 Hz,2H), 4.48–4.38 (m,1H), 4.32–4.18 (m,2H), 3.45–3.20 (m,2H), 3.20–3.05 (m,2H), 2.36 (hept d, J=3.8 Hz,7.0 Hz, 1H), 0.91 (d, J=7.0 Hz, 3H), 0.86 (d, J=7.0 Hz, 3H); FAB mass spectrum, m/z: 458 (M+H)$^+$, 424 (M−Cl)$^+$.

(f) 3-{4-tert-Butoxy-4-oxo-2(R)-{{2-[(2,2,2-trichloroethoxy)carbonylamino]-4-thiazolyl}methyl}butyl}-4(S)-(1-methylethyl)-2-oxazolidinone:

A solution of the product of previous section (e) (615 mg, 1.35 mmol) in THF (5.0 mL) was added to a cold (−78°) solution of sodium bis-(trimethylsilyl)amide (3.1 mL, 3.1 mmol) in THF (3.0 mL). The mixture was stirred at −78° for 40 min. A solution of tert-butyl 2-bromoacetate (435 μL, 2.69 mmol) in THF (1 mL) was added to the mixture which was then stirred at −78° for 1.5 h. The mixture was quenched with a saturated aqueous solution of $NH_4Cl$ and diluted with EtOAc. The organic phase was separated, washed with $H_2O$ and brine, dried ($MgSO_4$) and evaporated. The residue was purified by flash chromatography ($SiO_2$, eluent: EtOAc-hexane, 1:4) to give the desired product (459 mg, 60%), $^1H$ NMR (400 MHz, CDCl$_3$) δ10,.50 (broad s,1H), 6.70 (s,1H), 4.92 (q$_{AB}$, J$_{AB}$=12.1 Hz, 2H), 4.55–4.40 (m,1H), 4.40–4.30 (m,1H), 4.20–4.05 (m,2H), 3.10–2.90 (m,2H), 2.85–2.65 (m,1H), 2.47–2.38 (m,1H), 2.32 (hept d, J=3.8 Hz,7.0 Hz, 1H), 1.39 (s,9H), 0.89 (d, J=7.0 Hz,3H), 0.87 (d, J=7.0 Hz, 3H); FAB mass spectrum, m/z: 572 (M+H)$^+$.

(g) The amino acid, 4-{[1(S)-(cyclohexylmethyl)2(R),3(S)-dihydroxy-5-methylhexyl]amino}-4-oxo-3(R)-{ {2-[(2,2,2-trichloroethoxy)carbonylamino]-4-thiazolyl}methyl}butanoic Acid:

A solution of the product of section (f) of this example (57.5 mg, 0.10 mmol) in THF (1.5 mL) and H$_2$O (0.5 mL) was cooled to 0°. A 30% aqueous solution of H$_2$O$_2$ (91.3 μL, 0.80 mmol of H$_2$O$_2$) and lithium hydroxide monohydrate (8.5 mg, 0.20 mmol) were added serially to the cooled solution. The mixture was stirred at 0° for 5 min and then at room temperature for 2.5 h. Excess H$_2$O$_2$ was quenched by the addition of a 1.5M aqueous solution of Na$_2$SO$_3$. The resulting mixture was diluted with H$_2$O and washed with CH$_2$Cl$_2$ (3×). The aqueous layer was rendered acidic with 1N aqueous HCl and extracted with EtOAc (3×). The combined EtOAc extracts were washed with brine, dried (MgSO$_4$) and concentrated to dryness to yield the desired monoprotected dicarboxylic acid, i.e. the 4-tert-butyl ester of 2(R)-{{2-[(2,2,2-trichloroethoxy)carbonylamino]-4-thiazolyl}methyl}butanedioic acid. The monoprotected dicarboxylic acid was used for the following coupling step without purification.

The monoprotected dicarboxylic acid (0.10 mmol) was dissolved in DMF (1 mL). DIPEA (43.8 μL, 0.25 mmol), BOP•PF$_6$ (48 mg, 0.11 mmol) and 2(S)-amino-1-cyclohexyl- 6-methyl-3 (R), 4 (S)-heptanediol hydrochloride (30 mg, 0.11 mmol) were added to the solution. The pH of the mixture was adjusted to pH 8.5 with DIPEA. The resulting mixture was stirred at room temperature for 2.5 h. Thereafter, the mixture was diluted with EtOAc. The organic phase was washed with 1N aqueous HCl, a saturated aqueous solution of NaHCO$_3$, H$_2$O and brine, dried (MgSO$_4$) and evaporated to dryness. The residue was purified by flash chromatography (SiO$_2$, eluent: EtOAc-hexane, 3:7) to give the tert-butyl ester of the desired amido acid of formula 4 (27.9 mg, 40%); $^1$H NMR (400 MHz, CDCl$_3$) δ10.23 (broad s,1H), 6.66–6.59 (m,2H), 4.85 (q$_{AB}$, J$_{AB}$=11.8 Hz, 2H), 4.55–4.40 (m,1H), 4.30–4.15 (m,1H), 3.55–3.43 (m,1H), 3.35–3.05 (m,3H), 3.05–2.85 (m,1H), 2.80–2.65 (m,1H), 2.43–2.33 (m,1H), 2.00–1.80 (m,1H), 1.80–1.70 (m,1H), 1.70–1.00 (m,11H), 1.44 (s,9H), 1.00–0.70 (m,3H), 0.94 (d, J=6.6 Hz, 3H), 0.85 (d, J=6.6 Hz, 3H).

The preceding tert-butyl ester (190 mg, 0.28 mmol) was dissolved in a solution of TFA-CH$_2$Cl$_2$ (1:1, 5 mL) and the resulting solution was allowed to stand at room temperature for 1 h. The solution was evaporated to dryness to give the desired amido acid of formula 4 wherein R$^2$ is {2-[(2,2,2-trichloroethoxy)carbonylamino]-4-thiazolyl}methyl and B is 1(S)-(cyclohexylmethyl)-2(R),3(S)-dihydroxy-5-methylhexylamino. The compound was used without further purification for ensuing coupling reactions.

D. 4-{[1(S)-(Cyclohexylmethyl-2(R),3(S)-dihydroxy5-methylhexyl]amino}-4-oxo-3(R) -(4-thiazolylmethyl)butanoic Acid (a) 4(S)-(1-Methylethyl)-3-[1-oxo-3-(4-thiazolyl)propyl-2-oxazolidinone:

Thioformamide (8.52 g, 0.14 mol) was added to a stirred solution of the bromoketone of section C(c) of this example (7.12 g, 23.3 mmol) in THF (120 mL). The mixture was stirred at room temperature for 5 h. Thereafter, the mixture was diluted with Et$_2$O, washed with 10% (w/v) aqueous NaHCO$_3$ and then H$_2$O, dried (MgSO$_4$) and concentrated to dryness under reduced pressure to give 4(S)-(1-methylethyl)-3-[1-oxo-3-(4-thiazolyl)propyl]-2-oxazolidinone (3.8 g, 61%); $^1$H NMR (CDCl$_3$) δ8.75 (s,1H), 7.05 (s,1H), 4.47–4.40 (m,1H), 4.30–4.16 (m,2H), 3.46–3.36 (m,2H), 3.28–3.17 (m,2H), 2.45–2.28 (m,1H), 0.90 (d, J=7.1 Hz, 3H), 0.86 (d, J=6.9 Hz, 3H).

(b) 3-[4-tert-Butoxy-1,4-dioxo-2(R)-(4-thiazolylmethyl)butyl]-4(S)-(1-methylethyl)-2-oxazolidinone:

The product of the preceding section (825 mg, 3.07 mmol) was stereoselectively alkylated with tert-butyl 2-bromoacetate according to the procedure described in section C(f) of this example to give a mixture of the desired 3-[4-tert-butoxy-1,4-dioxo-2(R)-(4-thiazolylmethyl)butyl ]-4 (S)-(1-methylethyl)-2-oxazolidinone (Rf=0.25, eluent: EtOAc-hexane, 1:2) and its corresponding 2(S)-epimer (Rf= 0.41, eluent: EtOAc-hexane, 1:2 ) in a 7:1 ratio, respectively. Flash chromatography (SiO$_2$, eluent: EtOAc-hexane, 1:2) yielded the pure desired compound as a white solid (882 mg, 75%), $^1$H NMR (CDCl$_3$) δ8.75 (s,1H), 7.14 (s,1H), 4.62–4.5 (m,1H), 4.50–4.40 (m,1H), 4.29–4.20 (m,2H), 3.19 (dd, J=6.4 Hz,14.2 Hz, 1H), 3.02 (dd, J=7.5 Hz,14.2 Hz, 1H), 2.84 (dd, J=9.8 Hz, 16.6 Hz, 1H), 2.49 (dd, J=4.7 Hz,16.6 Hz, 1H), 1.41 (s,9H), 0.95 (d, J=6.8 Hz, 3H), 0.92 (d, J=7.0 Hz, 3H).

(c) 4-{[1(S)-(Cyclohexylmethyl)-2(R),3(S)-dihydroxy-5-methylhexyl]amino}-4-oxo-3(R)-(4-thiazolylmethyl)butanoic Acid:

The desired 2-oxazolidinone of the previous section (4.02 g, 10.5 mmol) was reacted with lithium hydroxide-hydrogen peroxide according to the procedure of section C(g) of this example to give the monoprotected dicarboxylic acid of formula 2, i.e. the 4-tert-butyl ester of 2(R)-(4-thiazolylmethyl)butanedioic acid. Subsequent coupling of the latter compound (2.83 g, 10.4 mmol) with 2(S)-amino-1-cyclohexyl-6-methyl-3(R), 4(S)-heptanediol hydrochloride (3.21 g, 11.5 mmol) according to the coupling procedure section C(g) of this example gave the desired protected amido acid of formula 3 wherein W$^1$ is tert-butoxy, R$^2$ is 4-thiazolylmethyl and B is 1(S)-(cyclohexylmethyl)- 2(R), 3(S)-dihydroxy-5-methylhexyl, as a white solid (3.75 g, 72%); $^1$H NMR (CDCl$_3$) δ8.70 (s, 1H), 7.10 (s,1H), 5.96 (d, J=8.3 Hz, 1H), 4.40–4.25 (m,2H), 3.40–2.70 (m,6H), 2.40 (dd, J=4.4 Hz,16.8 Hz, 1H), 1.95–1.10 (m,17H), 1.40 (s,9H), 0.90 (d, J=6.6 Hz, 3H), 0.80 (d, J=6.4 Hz, 3H). The latter compound was deprotected as follows: The compound (3.7 g, 7.45 mmol) was dissolved in CH$_2$Cl$_2$ (30 mL). Under a N$_2$ atmosphere at 0°, TFA (6 mL) was added to the solution. The reaction mixture was stirred for 5.5 h. At this point, another portion of TFA (6 mL) was added to the reaction mixture at 0°. The mixture was stirred at room temperature for 3 h. Thereafter, the mixture was diluted with Et$_2$O and concentrated to dryness under reduced pressure to give the desired amido acid (4.70 g); FAB mass spectrum, m/z: 441 (M+H)$^+$. The compound was used without further purification for ensuing coupling steps.

EXAMPLE 3

N$^4$-benzyl-N$^4$-[(1-hydroxycyclohexyl)methyl]-N$^1$-[1(S)-(cyclohexylmethyl)- 2(R),3(S)-dihydroxy-5-methylhexyl]-2(R)-(cyclopropylmethyl) butanediamide N-methylmorpholine (2.0 mL, 2.7 mmol), 1-{[(phenylmethyl)amino]methyl}cyclohexanol (107 mg, 0.49 mmol, described in example 1, section D) and BOP•PF$_6$ (218 mg, 0.49 mmol were added serially to a cooled (0°) solution of 3(R)-(cyclopropylmethyl)-4-{[1(S)-cyclohexylmethyl)-

2(R), 3(S)-dihydroxy-5-methylhexyl] amino}-4-oxobutanoic acid (179 mg, 0.45 mmol, described in example 2, section A) in dry DMF (5 mL). The reaction mixture was allowed to warm to room temperature. After being stirred for 1 h, the reaction mixture was poured into $H_2O$. The resulting mixture was extracted with EtOAc (3×10 mL). The EtOAc extract was dried ($Na_2SO_4$) and concentrated to dryness under reduced pressure. The residual oil was purified by chromatography ($SiO_2$, eluent: hexane-EtOAc, 1:1) and crystallized from EtOAc/hexane to give the title compound as a white solid (210 mg, 39%); $^1H$ NMR (400 MHz, DMSO-$d_6$) (2:1 mixture of rotamers) δ7.66 and 7.61 (d, J=9.6 Hz, 1H), 7.35 (t, J=7.5 Hz, 2H), 7.27 (d, J=6.9 Hz, 1H), 7.15 (d, J=7.2 Hz, 2H), 4.82 (d,2H), 4.71–4.59 (m,2H), 4.45 and 4.36 (s,1H), 4.07 (m,1H), 3.36 (d, J=14.1 Hz, 1H), 3..23 (d, J=14.0 Hz, 1H), 3.10–3.04 (m,1H), 2.95–2 75 (m,2H), 2 55 (dd, $J^1$=7.7 Hz, $J^2$=16.1 Hz, 1H), 2.37 (dd, $J^1$=6.3 Hz, $J^2$=16.5 Hz , 1H), 1.75 (m,1H), 1.67–1.25 (m,20H), 1.22–1.00 (m,7H), 0.86 and 0.85 (d, J=6.6 Hz, 3H), 0.74 (t, J=6.5 Hz, 3H), 0.68 and 0.58 (m,1H), 0.36 and 0.31 (d, J=8.1 Hz, 1H), 0.08–0.08 (m,2H); FAB mass spectrum, m/z: 600 (M+H)$^+$; $[\alpha]_D^{24}$–36.6° (c 1.07, $CHCl_3$).

EXAMPLE 4

$N^4$-benzyl-$N^4$-[(1-hydroxycyclohexyl)methyl]-$N^1$-[1(S)-(cyclohexylmethyl)- 2(R),3(S) -dihydroxy-5-methylhexyl]-2(R)-(1H-imidazol-4-ylmethyl)butanediamide 4-{[1(S)-(cyclohexylmethyl)-2(R),3(S)-dihydroxy-5-methylhexyl]amino}-4-oxo-3(R)-{[(1-triphenylmethyl)-1H-imidazol-4-yl]methyl}butanoic acid (described in example 2, section B) and 1-[(phenylmethyl)amino]methyl}cyclohexanol (described in example 1, section D) were coupled by the procedure described in example 3 (using DIPEA instead of N-methylmorpholine as the base) to give $N^4$-benzyl-$N^4$-[(1-hydroxycyclohexyl)methyl]-$N^1$-[1(S)-(cyclohexylmethyl)-2(R),3(S)-dihydroxy-5-methyl-hexyl]-2(R)-{[1-(triphenylmethyl)-1H-imidazol-4-yl]-methyl}butanediamide. Thereafter, a solution of the latter compound (53 mg, 0.061 mmol) in $CH_2Cl_2$ (0.9 mL) was cooled to 0°. TFA (0.1 mL) was added to the cooled solution. The mixture was stirred at 0° for 45 min, at room temperature for 4 h, and then recooled to 0°. A saturated aqueous solution of $NaHCO_3$ was added dropwise until the pH of the solution was 10. The mixture was diluted with EtOAc. The organic phase was separated, washed with brine, dried ($Na_2SO_4$) and concentrated to dryness under reduced pressure. The residue was purified by chromatography [$SiO_2$, eluent: chloroform-MeOHH—$CH_3COOH$—$H_2O$, respectively 80:20:2:1/chloroform (6:4)] to give the title compound as a white solid (15 mg, 39%); $^1H$ NMR (400 MHz, DMSO-$d_6$) (2:1 mixture of rotamers) δ7.90–7.75 (m,1H), 7.65 and 7.61 (d, J=9.0 Hz, 1H), 7.33 (t, J=7.2Hz, 2H), 7.30–7.10 (m,5H), 6.94 and 6.87 (s,1H), 4.77 (s,2H), 4.82–4.61 (m,2H), 4.46 and 4.35 (1s,1H), 4.15–4.00 (m,1H), 3.39 (d, J=13.2 Hz, 1H), 3.11 (d,12.6 Hz, 1H) 2.98–2.91 (t, J=8.7 Hz, 1H), 2.85–2.55 (m,2H), 2.34 (dd, $J^1$=4.5 Hz, $J^2$=15.6 Hz, 1H), 1.78–1.00 (m,28H, 0.84 (d, J=6.6 Hz, 3H), 0.72 (t, J=6.3 Hz, 3H); FAB mass spectrum, m/z: 625 (M+H)$^+$.

EXAMPLE 5

$N^4$-benzyl-$N^4$-[(1-hydroxycyclohexyl)methyl ]-$N^1$-[1(S)-(cyclohexylmethyl)- 2(R),3(S)-dihydroxy-5-methylhexyl]-2(R)-(4-thiazolylmethyl)butanediamide 4{[1(S)-(Cyclohexylmethyl)-2(R),3(S)-dihydroxy-5-methylhexyl]amino}-4-oxo-3(R)-(4-thiazolylmethyl)-butanoic acid (61 mg, 0.14 mmol, described in example 2, section D) was coupled with 1-{[(phenylmethyl)amino]methyl}cyclohexanol (31 mg, 0.14 mmol, described in example 1, section D) according to the procedure described in example 3 to give the title compound (41 mg, 17%); $^1H$ NMR (400 MHz, DMSO-$d_6$) (2.2:1 mixture of rotamers) δ9.00 and 8.95 (d, J=1.8 Hz, 1H), 7.76 and 7.71 (d, J=8.9 Hz, 1H), 7.36–7.20 (m,4H), 7.15 and 7.10 (d, J=7.2 Hz,2H), 4.77 (broad s,2H), 4.62–4.58 (m,2H), 4.43 and 4.34 (s,1H), 4.13–4.02 (m,1H), 3.17 (d, J=13.8 Hz, 1H), 3.09–2.76 (m,5H), 2.62 (dd, $J^1$=8.1 Hz, $J^2$=16.5 Hz, 1H), 2.32 (dd, $J^1$=5.4 Hz, $J^22$ =16.1 Hz, 1H), 1.68–1.25 (m,21H), 1.22–1.03 (m,6H), 0.85 and 0.84 (d, J=6.6 Hz, 3H), 0.73 (t, J=5.4 Hz,3H); FAB mass spectrum , m/z: 642 (M+H)$^+$.

By applying the appropriate intermediates, the serial coupling and deprotection procedure illustrated by examples 2, 3, 4 and 5 can be used to prepare other compounds of formula 1, such a those exemplified in the table of the following example.

EXAMPLE 6

Plasma Renin Assay

The ability of the compounds of formula 1 to inhibit human renin can be demonstrated in the plasma renin assay. The assay is performed as follows: The test compound (i.e. the inhibitor) is dissolved in dimethylsulfoxide (1 mM stock solution) and diluted with an aqueous buffer solution of 270 mM 2-(N-morpholino)ethanesulfonic acid and 1% human serum albumin (pH 5.85, also containing dimercaprol and 8-hydroxyquinoline sulfate in accordance with the instructions of the RIA kit noted below) to give an assay mixture in which the final dimethylsulfoxide content is 1% (v/v).

A human plasma pool is used as the source of both the substrate (angiotensinogen) and the enzyme (renin). The reaction is initiated by the addition of 50 μL of human plasma pool to 50 μL of various concentrations of inhibitor in the 1% dimethylsulfoxide assay buffer. The plasma renin activity is measured by the amount of angiotensin I generated at pH 6.0 following a 2 h incubation at 37°.

Quantitation of angiotensin I is performed by radioimmunoassay (RIA kit from New England Nuclear-Dupont, Mississauga, ON, Canada). The enzymatic activity of renin is expressed in ng of angiotensin I generated (/mL/2 h). The extent of inhibition of the reaction is determined from the amount of angiotensin 2 generated in reference to a control prepared without inhibitor. Nonlinear regression analysis is used to calculate the $IC_{50}$ values, i.e. the molar concentration of the test compound required to cause a 50% inhibition of the enzyme activity.

The compounds of formula 1 exhibited $IC_{50}$'s in the range of $10^{-6}$ to $10^{-9}$ molar in this assay. The following table exemplifies results obtained for compounds of formula 1.

TABLE

| Compound of Formula 1 | FAB/MS (M + H)$^+$ | $IC_{50}$ (nM) |
| --- | --- | --- |
| 1. $N^4$-benzyl-$N^4$-[(1-hydroxycyclohexyl)-methyl]-$N^1$-[1(S)-(cyclohexylmethyl)-2(R),3(S)-dihydroxy-5-methylhexyl]-2(R)-(cyclopropylmethyl)butanediamide | 600 | 36 |
| 2. $N^4$-benzyl-$N^4$-[(1-hydroxycyclohexyl)-methyl]-$N^1$-[1(S)-(cyclohexylmethyl)-2(R),3(S)-dihydroxy-5-methylhexyl]-2(R)-propylbutanediamide | 587 | 27 |

TABLE-continued

| Compound of Formula 1 | FAB/MS (M + H)+ | IC$_{50}$ (nM) |
|---|---|---|
| 3. N$^4$-[(1-hydroxycyclohexyl)methyl]-N$^4$-[(4,5-methylenedioxyphenyl)methyl]-N$^1$-[1(S)-(cyclohexylmethyl)-2(R),3(S)-dihydroxy-5-methylhexyl]-2(R)-(cyclopropylmethyl)butanediamide | 643 | 21 |
| 4. N$^4$-[(1-hydroxycyclohexyl)methyl]-N$^4$-(2-pyridinylmethyl)-N$^1$-[1(S)-(cyclohexylmethyl)-2(R),3(S)-dihydroxy-5-methylhexyl]-2(R)-(cyclopropylmethyl)butanediamide | 600 | 36 |
| 5. N$^4$-[(1-hydroxycyclohexyl)methyl]-N$^4$-(2-hydroxyethyl)-N$^1$-[1(S)-(cyclohexylmethyl)-2(R),3(S)-dihydroxy-5-methylhexyl]-2(R)-(cyclopropylmethyl)butanediamide | 553 | 35 |
| 6. N$^4$-[(1-hydroxycyclohexyl)methyl]-N$^4$-methyl-N$^1$-[1(S)-(cyclohexylmethyl)-2(R),3(S)-dihydroxy-5-methylhexyl]-2(R)-(cyclopropylmethyl)butanediamide | 523 | 38 |
| 7. N$^4$-[(1-hydroxycyclohexyl)methyl]-N$^4$-[2-(2-pyridinyl)ethyl]-N$^1$-[1(S)-(cyclohexylmethyl)-2(R),3(S)-dihydroxy-5-methylhexyl]-2(R)-(cyclopropylmethyl)butanediamide | 614 | 53 |
| 8. N$^4$-[(1-hydroxycycloheptyl)methyl]-N$^4$-(2-pyridinylmethyl)-N$^1$-[1(S)-(cyclohexylmethyl)-2(R),3(S)-dihydroxy-5-methylhexyl]-2(R)-(cyclopropylmethyl)butanediamide | 614 | 65 |
| 9. N$^4$-(R)-(2-hydroxy-2-phenylethyl)-N$^1$-[1(S)-(cyclohexylmethyl)-2(R),3(S)-dihydroxy-5-methylhexyl]-2(R)-(cyclopropylmethyl)butanediamide | 517 | 72 |
| 10. N$^4$-(R,S)-(2-hydroxy-2-phenylethyl)-N$^1$-[1(S)-(cyclohexylmethyl)-2(R),3(S)-dihydroxy-5-methylhexyl]-2(R)-(cyclopropylmethyl)butanediamide | 517 | 74 |
| 11. N$^4$-benzyl-N$^4$-(R)-(2-hydroxy-2-phenylethyl)-N$^1$-[1(S)-(cyclohexylmethyl)-2(R),3(S)-dihydroxy-5-methylhexyl]-2(R)-(cyclopropylmethyl)butanediamide | 607 | 110 |
| 12. N$^4$-benzyl-N$^4$-(R,S)-(2-hydroxy-2-phenylethyl)-N$^1$-[1(S)-(cyclohexylmethyl)-2(R),3(S)-dihydroxy-5-methylhexyl]-2(R)-(cyclopropylmethyl)butanediamide | 607 | 71 |
| 13. N$^4$(R)-[1-(hydroxymethyl)-2-phenylethyl]-N$^1$-[1(S)-(cyclohexylmethyl)-2(R),3(S)-dihydroxy-5-methylhexyl]-2(R)-(cyclopropylmethyl)butanediamide | 531 | 89 |
| 14. N$^4$-(S)-[1-(hydroxymethyl)-2-phenylethyl]-N$^1$-[1(S)-(cyclohexylmethyl)-2(R),3(S)-dihydroxy-5-methylhexyl]-2(R)-(cyclopropylmethyl)butanediamide | 531 | 79 |
| 15. N$^4$-[(1-hydroxycyclohexyl)methyl]-N$^4$-(1H-imidazol-2-ylmethyl)-N$^1$-[1(S)-(cyclohexylmethyl)-2(R),3(S)-dihydroxy-5-methylhexyl]-2(R)-(cyclopropylmethyl)butanediamide | 589 | 80 |
| 16. N$^4$-(cyclopropylmethyl)-N$^4$-[(1-hydroxycyclohexyl)methyl]-N$^1$-[1(S)-(cyclohexylmethyl)-2(R),3(S)-dihydroxy-5-methylhexyl]-2(R)-(cyclopropylmethyl)butanediamide | 563 | 89 |
| 17. N$^4$-[(1-hydroxycyclohexyl)methyl]-N$^1$-[1(S)-(cyclohexylmethyl)-2(R),3(S)-dihydroxy-5-methylhexyl]-2(R)-(cyclopropylmethyl)butanediamide | 509 | 94 |
| 18. N$^4$-[2(S)-hydroxy-1(S)-(hydroxymethyl)-2-phenylethyl]-N$^1$-[1(S)-(cyclohexylmethyl)-2(R),3(S)-dihydroxy-5-methylhexyl]-2(R)-(cyclopropylmethyl)butanediamide | 547 | 95 |
| 19. N$^4$-[(1-hydroxy-4-oxocyclohexyl)methyl]-N$^4$-(2-pyridinylmethyl)-N$^1$-[1(S)-(cyclohexylmethyl)-2(R),3(S)-dihydroxy-5-methylhexyl]-2(R)-(cyclopropylmethyl)butanediamide | 614 | 100 |
| 20. N$^4$-(R)-and N$^4$-(S)-(2-cyclohexyl-2-hydroxyethyl)-N$^1$-[1(S)-(cyclohexylmethyl)-2(R),3(S)-dihydroxy-5-methylhexyl]-2(R)-(cyclopropylmethyl)butanediamide | 523, 523 | 115, 150 |
| 21. N$^4$-benzyl-N$^4$-(2-hydroxy-2-methylpropyl)-N$^1$-[1(S)-(cyclohexylmethyl)-2(R),3(S)-dihydroxy-5-methylhexyl]-2(R)-(cyclopropylmethyl)butanediamide | 559 | 130 |
| 22. N$^4$-[2(R,S)-hydroxy-2-(2-pyridinyl)ethyl]-N$^1$-[1(S)-(cyclohexylmethyl)-2(R),3(S)-dihydroxy-5-methylhexyl]-2(R)-(cyclopropylmethyl)butanediamide | 518 | 170 |
| 23. N$^4$-[(1-hydroxycyclohexyl)methyl]-N$^4$-[2-(dimethylamino)-2-oxoethyl]-N$^1$-[1(S)-(cyclohexylmethyl)-2(R),3(S)-dihydroxy-5-methylhexyl]-2(R)-(cyclopropylmethyl)butanediamide | 594 | 16 |
| 24. N$^4$-[(1-hydroxycyclohexyl)methyl]-N$^4$-[2-(dimethylamino)-2-oxoethyl]-N$^1$-[1(S)-(cyclohexylmethyl)-2(R),3(S)-dihydroxy-5-methylhexyl]-2(R)-(1H-imidazol-4-ylmethyl)-butanediamide | 620 | 1.8 |
| 25. N$^4$-(cyclohexylmethyl)-N$^4$-[(1-hydroxycyclohexyl)methyl]-N$^1$-[1(S)-(cyclohexylmethyl)-2(R),3(S)-dihydroxy-5-methylhexyl]2(R)-(cyclopropylmethyl)butanediamide | 605 | 79 |
| 26. N$^4$-[(1-hydroxycyclohexyl)methyl]-N$^4$-(3-pyridinylmethyl)-N$^1$-[1(S)-(cyclohexylmethyl)-2(R),3(S)-dihydroxy-5-methylhexyl]-2(R)-(cyclopropylmethyl)butanediamide | 600 | 26 |
| 27. N$^4$-benzyl-N$^4$-[(1-hydroxycyclohexyl)methyl]-N$^1$-[1(S)-(cyclohexylmethyl)-2(R),3(S)-dihydroxy-5-methylhexyl]-2(R)-(4-thiazolylmethyl)butanediamide | 642 | 15 |
| 28. N$^4$-benzyl-N$^4$-[(1-hydroxycyclohexyl)methyl])-N$^1$-[1(S)-(cyclohexylmethyl)-2(R),3(S)-dihydroxy-5-methylhexyl]-2(R)-(1H-imidazol-4-ylmethyl)butanediamide | 625 | 53 |
| 29. N$^4$-[(1-hydroxycyclohexyl)methyl]-N$^4$-(4-pyridinylmethyl)-N$^1$-[1(S)-(cyclohexylmethyl)-2(R),3(S)-dihydroxy-5-methylhexyl]-2(R)-cyclopropylmethyl)butanediamide | 600 | 31 |
| 30. N$^4$-[(1-hydroxycyclohexyl)methyl]-N$^4$-methyl-N$^1$-[1(S)-(cyclohexylmethyl)-2(R),3(S)-dihydroxy-5-methylhexyl]-2(R)-(4-thiazolylmethyl)butanediamide | 566 | 12 |
| 31. N$^4$-(cyclohexylmethyl)-N$^4$-(2-hydroxyethyl)-N$^1$-[1(S)-(cyclohexylmethyl)-2(R),3(S)-dihydroxy-5-methylhexyl]-2(R)-(cyclopropylmethyl)butanediamide | 537 | 100 |
| 32. N$^4$-(cyclohexylmethyl)-N$^4$-(2-hydroxy-2-methylpropyl)-N$^1$-[1(S)-(cyclohexylmethyl)-2(R),3(S)-dihydroxy-5-methylhexyl]-2(R)-(cyclopropylmethyl)butanediamide | 565 | 46 |
| 33. N$^4$-[(1-hydroxycyclohexyl)methyl]-N$^4$-[(3,4-methylenedioxyphenyl)methyl]-N$^1$-[1(S)-(cyclohexylmethyl)- | 686 | 11 |

TABLE-continued

| Compound of Formula 1 | FAB/MS (M + H)+ | IC50 (nM) |
|---|---|---|
| 2(R),3(S)-dihydroxy-5-methylhexyl]-2(R)-(4-thiazolylmethyl)butanediamide | | |
| 34. N4-[(1-hydroxycyclohexyl)methyl]-N4-[2-(dimethylamino)-2-oxoethyl]-N1-[1(S)-(cyclohexylmethyl)-2(R),3(S)-dihydroxy-5-methylhexyl]-2(R)-(4-thiazolylmethyl)butanediamide | 637 | 1.6 |
| 35. N4-[(1-hydroxycyclohexyl)methyl]-N4-methyl-N1-[1(S)-(cyclohexylmethyl)-2(R),3(S)-dihydroxy-5-methylhexyl]-2(R)-(1H-imidazol-4-ylmethyl)-butanediamide | 549 | 67 |
| 36. N4-(cyclohexylmethyl)-N4-(2-hydroxy-2-methylpropyl)-N1-[1(S)-(cyclohexylmethyl)-2(R),3(S)-dihydroxy-5-methylhexyl]-2(R)-(4-thiazolylmethyl)butanediamide | 608 | 7.1 |
| 37. N4-[(1-hydroxycyclohexyl)methyl]-N4-(2-hydroxyethyl)-N1-[1(S)-(cyclohexylmethyl)-2(R),3(S)-dihydroxy-5-methylhexyl]-2(R)-(4-thiazolylmethyl)butanediamide | 596 | 16 |
| 38. N4-[(1-hydroxycyclohexyl)methyl]-N4-[2-(dimethylamino)-2-oxoethyl]-N1-[1(S)-(cyclohexylmethyl)-2(S)-hydroxy-2-(1,5,5-trimethyl-2-oxopyrrolidin-3(S)-yl)ethyl]-2(R)-(cyclopropylmethyl)butanediamide | 633 | 15 |
| 39. N4-(cyclohexylmethyl)-N4-[2(R or S)-hydroxypropyl]-N1-[1(S)-(cyclohexylmethyl)-2(R),3(S)-dihydroxy-5-methylhexyl]-2(R)-(4-thiazolylmethyl)butanediamide[rf = 0.12; tlc: SiO2 (EtOAc)] | 594 | 8.7 |
| 40. N4-(cyclohexylmethyl)-N4-[2(S or R)-hydroxypropyl]-N1-[1(S)-(cyclohexylmethyl)-2(R),3(S)-dihydroxy-5-methylhexyl]-2(R)-(4-thiazolylmethyl)butanediamide[rf = 0.19; tlc: SiO2 (EtOAc)] | 594 | 11 |
| 41. N4-(cyclohexylmethyl)-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 623 | 9 |
| 42. N4-[2-cyclohexyl-2-(R,S)-hydroxyethyl]-N4-[2-(dimethylamino)-2-oxoethyl]-N1-[1(S)-(cyclohexylmethyl)-2(R),3(S)-dihydroxy-5-methylhexyl]-2(R)-(4-thiazolylmethyl)butanediamide | 651 | 16 |
| 43. N4-(cyclohexylmethyl)-N4-(2-hydroxy-2-methylpropyl)-N1-[1(S)-(cyclohexylmethyl)-2(R),3(S)-dihydroxy-5-methylhexyl]-2(R)-(1H-imidazol-4-ylmethyl)butanediamide | 591 | 14 |
| 44. N4-[2-(dimethylamino)-2-oxoethyl]-N4-[2(R,S)-hydroxy-2-phenylethyl]-N1-[1(S)-(cyclohexylmethyl)-2(R),3(S)-dihydroxy-5-methylhexyl]-2(R)-(4-thiazolylmethyl)butanediamide | 645 | 10 |
| 45. N4-[2-cyclohexyl-1(R)-(hydroxymethyl)ethyl]-N1-[1(S)-cyclohexylmethyl]-2(R),3(S)-dihydroxy-5-methylhexyl]-2(R)-(4-thiazolylmethyl)butanediamide | 580 | 37 |
| 46. N4-[2-(dimethylamino)-2-oxoethyl]-N4-[(1-hydroxycyclohexyl)methyl]-N1-[1(S)-(cyclohexylmethyl)-2(R),3(S)-dihydroxy-5-methylhexyl]-2(R)-[(2-amino-4-thiazolyl)methyl]butanediamide | 652 | 1.3 |
| 47. N4-(cyclopentylmethyl)-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 609 | 7 |
| 48. N4-(cycloheptylmethyl)-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 637 | 5 |
| 49. N4-[(1-hydroxycyclohexyl)methyl]-N4-{2-{methyl[2-(2-pyridinyl)ethyl]amino}-2-oxoethyl}-N1-[1(S)-(cyclohexylmethyl)-2(R),3(S)-dihydroxy-5-methylhexyl]-2(R)-[(2-amino-4-thiazolyl)methyl]butanediamide | 743 | 2 |
| 50. N4-(cyclopentylmethyl)-N4-(2-hydroxy-2-methylpropyl)-N1-[1(S)-(cyclohexylmethyl)-2(R),3(S)-dihydroxy-5-methylhexyl]-2(R)-(4-thiazolylmethyl)butanediamide | 594 | 13 |
| 51. N4-(cycloheptylmethyl)-N4-(2-hydroxy-2-methylpropyl)-N1-[1(S)-(cyclohexylmethyl)-2(R),3(S)-dihydroxy-5-methylhexyl]-2(R)-(4-thiazolylmethyl)butanediamide | 622 | 5 |
| 52. N4-[(1-hydroxycyclohexyl)methyl]-N4-[2-(dimethylamino)-2-oxoethyl]-N1-[1(S)-(cyclohexylmethyl)-2(R),3(S)-dihydroxy-5-methylhexyl]-2(R)-(3-pyridinylmethyl)butanediamide | 631 | 33 |
| 53. N4-[(1-hydroxycycloheptyl)methyl]-N4-[2-(dimethylamino)-2-oxoethyl]-N1-[1(S)-(cyclohexylmethyl)-2(R),3(S)-dihydroxy-5-methylhexyl]-2(R)-[(2-amino-4-thiazolyl)methyl]-butanediamide | 666 | 2 |
| 54. N4-benzyl-N4-(2-hydroxy-2-methylpropyl)-N1-[1(S)-(cyclohexylmethyl)-2(R),3(S)-dihydroxy-5-methylhexyl]-2(R)-((2-amino-4-thiazolyl)methyl]-butanediamide | 617 | 26 |
| 55. N4-(2-furanylmethyl)-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 607 | 21 |
| 56. N4-[(1-hydroxycyclooctyl)methyl]-N4-[2-(dimethylamino)-2-oxoethyl]-N1-[1(S)-(cyclohexylmethyl)-2(R),3(S)-dihydroxy-5-methylhexyl]-2(R)-[(2-amino-4-thiazolyl)methyl]butanediamide | 680 | 1 |
| 57. N4-[(2-methylphenyl)methyl]-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 631 | 37 |
| 58. N4-(2-ethylbutyl)-N4-(2-hydroxy-2-methylpropyl)-N1-[1(S)-(cyclohexylmethyl)-2(R),3(S)-dihydroxy-5-methylhexyl]-2(R)-[(2-amino-4-thiazolyl)methyl]butanediamide | 611 | 15 |
| 59. N4-[(1-hydroxycycloheptyl)methyl]-N4{2-{methyl[2-(2-pyridinyl)ethyl]amino}-2-oxoethyl}-N1-[1(S)-(cyclohexylmethyl)-2(R),3(S)-dihydroxy-5-methylhexyl]-2(R)-[(2-amino-4-thiazolyl)methyl]butanediamide | 757 | 1.5 |
| 60. N4-(cyclohexylmethyl)-N4-(2-oxopropyl)-N1-[1(S)-(cyclohexylmethyl)-2(R),3(S)-dihydroxy-5-methylhexyl]-2(R)-(4-thiazolylmethyl)butanediamide | 592 | 2 |

TABLE-continued

| Compound of Formula 1 | FAB/MS (M + H)+ | IC$_{50}$ (nM) |
| --- | --- | --- |
| 61. N$^4$-(cyclohexylmethyl)-N$^4$-(3-methyl-2-oxobutyl)-N$^1$-[1(S)-(cyclohexyl-methyl)-2(R),3(S)-dihydroxy-5-methylhexyl]-2(R)-(4-thiazolylmethyl)butanediamide | 620 | 9 |
| 62. N$^4$-[(1-methoxycyclohexyl)methyl]-N$^4$-{2-{methyl[2-(2-pyridinyl)ethyl]-amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide | 757 | 2 |
| 63. N$^4$-(cyclohexylmethyl)-N$^4$-(3-methyl-2-oxobutyl)-N$^1$-(1(S)-(cyclohexyl-methyl)-2(R),3(S)-dihydroxy-5-methylhexyl]-2(R)-[(2-amino-4-thiazolyl)methyl]butanediamide | 635 | 5 |

Other compounds of formula 1 include:

N$^4$-[(1-hydroxycyclohexyl)methyl]-N$^4$-(2-hydroxy-2-methylpropyl)-N$^1$-[1(S)-(cyclohexylmethyl)-2(R), 3(S)-dihydroxy- 5-methylhexyl]-2(R)-(4-thiazolylmethyl)butanediamide, N$^4$-(cycloheptylmethyl)-N$^4$-(2-oxopropyl)-N$^1$-[1(S)-(cyclohexylmethyl)- 2(R), 3(S)-dihydroxy-5-methylhexyl]-2(R)-(4-thiazolylmethyl)butanediamide, N$^4$-[2-(dimethylamino)-2-oxoethyl]-N$^4$-[(1-methoxycyclohexyl)methyl]-N$^1$-[1(S)-(cyclohexylmethyl)-2(R),3(S) -dihydroxy-5-methylhexyl]-2(R)-[(2-amino-4-thiazolyl) methyl]butanediamide, N$^4$-(cyclohexylmethyl)-N$^4$-[2(R or S)-hydroxy-3-methylbutyl]-N$^1$-[1(S)-(cyclohexylmethyl)-2(R), 3(S)-dihydroxy-5-methylhexyl ]-2 (R)-(4-thiazolylmethyl)butanediamide, N$^4$-(cyclohexylmethyl) -N$^4$-[2(R or S) -hydroxy-2-phenyl-ethyl]-N$^1$-[1(S)-(cyclohexylmethyl)-2(R),3(S)-dihydroxy- 5-methylhexyl]-2(R)-(4-thiazolylmethyl)butanediamide, N$^4$-[(1-hydroxycyclohexyl)methyl]-N$^4$-[2-(dimethylamino)-2-oxoethyl]-N$^1$-[1(S)-(cyclohexylmethyl)-2(S)-hydroxy- 3-cyclopropylpropyl]-2(S)-(2-thiazolylmethyl)butanediamide, N$^4$-[(1-methoxycyclohexyl)methyl]-N$^4$-{2-{methyl[2-(2-pyridinyl)ethyl]amino}-2-oxoethyl}-N$^1$-[1(S)-(cyclohexylmethyl)- 2(S)-hydroxy-3-cyclopropylpropyl]-2(R)-[(2-amino-4-thiazolyl)methyl]butanediamide, N$^4$-[(1-hydroxycyclohexyl)methyl]-N$^4$-(2-morpholino-2-oxoethyl)-N$^1$-[1(S)-(cyclohexylmethyl)-2(R)-hydroxy-3-(1-methylethoxy)-3-oxopropyl]-2(R)-(4-thiazolylmethyl)butanediamide, N$^4$-[(1-hydroxycyclohexyl)methyl]-N$^4$-{2-{methyl[2-(2-pyridinyl)ethyl]amino}-2-oxoethyl}-N$^1$-[1(S)-(cyclohexylmethyl)- 2(R)-hydroxy-3-(1-methylethoxy)-3oxopropyl]- 2(S)-(2-thiazolylmethyl)butanediamide, and N$^4$-(2-methoxy-2-methylpropyl)-N$^4$-(cyclohexylmethyl)-N$^1$-[1(S)-(cyclohexylmethyl)-2(R), 3(S)-dihydroxy-5-methylhexyl]- 2(R)-[(2-amino-4-thiazolyl)methyl]butanediamide.

We claim:

1. A compound of formula 1A

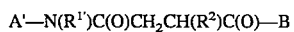

wherein A' is HO—CR$^5$(R$^6$)CH$_2$ wherein R$^5$ and R$^6$ together with the carbon atom to which they are attached form a 1,1-(lower cycloalkanediyl); R$^{1'}$ is R$^7$R$^8$NC(O)CH$_2$ wherein R$^7$ is hydrogen or lower alkyl and R$^8$ is lower alkyl; R$^2$ is Het-CH$_2$ wherein Het is an unsubstituted or mono-substituted thiazole ring wherein the substituent is selected from the group consisting of lower alkyl, lower alkoxy, halo, hydroxy, amino and lower alkylamino; B is a transition state analog of the formula NHCH(R$^{11}$)CH(OH)—Z wherein R$^{11}$ is lower alkyl or (lower cycloalkyl)methyl, and Z is lower alkyl or CH(OH)R$^{16}$ wherein R$^{16}$ is lower alkyl or lower cycloalkyl; with the provisos (1) that the asymmetric carbon atom bearing R$^{11}$ has the (S) configuration, (2) that when Z is lower alkyl, then the asymmetric carbon atom bearing the hydroxyl in the NHCH(R$^{11}$)CH(OH) radical has the (S) configuration, (3) that when Z is CH(OH)R$^{16}$ wherein R$^{16}$ is lower alkyl or lower cycloalkyl the asymmetric carbon atoms bearing the hydroxyls in the NHCH(R$^{11}$)CH(OH) and Z radicals have respectively the (R) and (S) configuration, and (4) that the carbon atom bearing R$^2$ has the (R) configuration; or a therapeutically acceptable acid addition salt thereof.

2. A compound as claimed in claim 1 wherein A' is HO—CR$^5$(R$^6$)CH$_2$ wherein R$^5$ and R$^6$ together with the carbon atom to which they are attached form a 1,1-(lower cycloalkanediyl); R$^{1'}$ is R$^7$R$^8$NC(O)CH$_2$ wherein R$^7$ is lower alkyl and R$^8$ is lower alkyl; R$^2$ is 2-thiazolylmethyl, 4-thiazolylmethyl, (2-methyl-4-thiazolyl)methyl, (2-amino-4-thiazolyl)methyl or [2-(methylamino)-4-thiazolyl]methyl; and B is as defined in claim 9, or a therapeutically acceptable acid addition salt thereof.

3. A compound as claimed in claim 2 wherein A' is HO—CR$^5$(R$^6$)CH$_2$ wherein R$^5$ and R$^6$ together with the carbon atom to which they are attached form a 1,1-cyclopentanediyl, 1,1-cyclohexanediyl, 1,1-cyclo-heptanediyl or 1,1-cyclooctanediyl; R$^{1'}$ is R$^7$R$^8$NC(O)-CH$_2$ wherein R$^7$ is methyl or ethyl and R$^8$ is methyl or ethyl; R$^2$ is 2-thiazolyl-methyl, 4-thiazolyl-methyl, (2-methyl-4-thiazolyl)methyl, (2-amino-4-thiazolyl)-methyl, [2-(methylamino)-4-thiazolyl]-methyl; and B is [1(S)-(2-methylpropyl)-2(R),3(S)-dihydroxy-5-methylhexyl]amino, [1(S)-(cyclohexyl-methyl)- 2(R),3(S)-dihydroxy-5-methylhexyl]amino, [1(S)-(2-methylpropyl)- 2(R),3(S)-dihydroxy-(3-cyclopropylpropyl)]amino or [1(S)-(cyclohexylmethyl)- 2(R),3(S)-dihydroxy-(3-cyclopropyl-propyl)]amino or 1(S)-(cyclohexylmethyl)- 2(R),3(S)-dihydroxy-(3-cyclopropylpropyl)]amino ; or a therapeutically acceptable acid addition salt thereof.

4. A compound as claimed in claim 3 wherein A' is (1-hydroxycyclohexyl)methyl, (1-hydroxycycloheptyl)-methyl or (1-hydroxycyclooctyl)methyl; R$^{1'}$ is 2-(dimethylamino)-2-oxoethyl; R$^2$ is 2-thiazolylmethyl, 4-thiazolylmethyl, (2-methyl-4-thiazolyl)methyl or (2-amino-4-thiazolyl)methyl; and B is [1(S)-(cyclo-hexylmethyl)-2(R), 3(S)-dihydroxy-5-methylhexyl]-amino or [1(S)-(cyclohexylmethyl)-2(R),3(S)-dihydroxy-(3-cyclopropylpropyl)]amino; or a therapeutically acceptable acid addition salt thereof.

5. A compound as claimed in claim 1 selected from the group consisting of:

N$^4$-[(1-hydroxycyclohexyl)methyl]-N$^4$-[2-(dimethylamino)- 2-oxoethyl]-N$^1$-[1(S)-(cyclohexylmethyl)- 2(R), 3(S)-dihydroxy-5-methylhexyl]-2(R)-(4-thiazolylmethyl)butanediamide N$^4$-[2-(dimethylamino)-2-oxoethyl]-N$^4$-[(1-hydroxy cyclohexyl)methyl]-N$^1$-[1(S)-(cyclohexylmethyl)- 2(R), 3(S)-dihydroxy-5-methylhexyl]-2(R)-[(2-amino-4-thiazolyl) methyl]butanediamide, N$^4$-[(1-hydroxycycloheptyl)methyl]-N$^4$-[2-dimethylamino-2-oxoethyl]-N$^1$-[1(S)-(cyclohexylmethyl)- 2(R),3(S)-dihydroxy-5-methylhexyl]-2(R)-[(2-amino-4-thiazolyl)methyl]butanediamide, and N$^4$-[(1-hydroxycyclooctyl)methyl]-N$^4$-[2-dimethylamino-2-oxoethyl]-N$^1$-[1(S)-(cyclohexylmethyl)- 2(R),3(S)-dihydroxy-5-methylhexyl]-2(R)-[(2-amino-4-thiazolyl)methyl]butanediamide.

6. A pharmaceutical composition comprising a compound as claimed in claim 1, or a therapeutically acceptable acid addition salt thereof, and a pharmaceutically acceptable carrier.

7. A method for treating renin-associated hypertension in a mammal which comprises administering to said animal a therapeutically effective amount of a compound as recited in claim 1 or a pharmaceutically acceptable acid addition salt thereof.

8. A method for treating congestive heart failure in a mammal which comprises administering to said animal a therapeutically effective amount of a compound as recited in claim 1 or a pharmaceutically acceptable acid addition salt thereof.

* * * * *